(12) United States Patent
Ogasawara

(10) Patent No.: US 10,666,888 B2
(45) Date of Patent: May 26, 2020

(54) ENDOSCOPE DEVICE AND ENDOSCOPE SYSTEM

(71) Applicant: OLYMPUS CORPORATION, Tokyo (JP)

(72) Inventor: Masamitsu Ogasawara, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 63 days.

(21) Appl. No.: 16/030,913

(22) Filed: Jul. 10, 2018

(65) Prior Publication Data

US 2018/0332249 A1 Nov. 15, 2018

Related U.S. Application Data

(63) Continuation of application No. PCT/JP2016/088103, filed on Dec. 21, 2016.

(30) Foreign Application Priority Data

Jan. 12, 2016 (JP) ................. 2016-003610

(51) Int. Cl.
*A61B 1/00* (2006.01)
*H04N 5/3745* (2011.01)
(Continued)

(52) U.S. Cl.
CPC ..... *H04N 5/37455* (2013.01); *A61B 1/00006* (2013.01); *A61B 1/00009* (2013.01);
(Continued)

(58) Field of Classification Search
CPC ............ H04N 5/37455; A61B 1/00009; A61B 1/00059

See application file for complete search history.

(56) References Cited

U.S. PATENT DOCUMENTS 9,876,974 B2 * 1/2018 Okawa ............... A61B 1/00009
2017/0303771 A1 * 10/2017 Sudo .................. A61B 1/00057

FOREIGN PATENT DOCUMENTS

JP 2006-116131 A 5/2006
JP 2006116131 A * 5/2006
(Continued)

OTHER PUBLICATIONS

International Search Report dated Mar. 28, 2017 issued in PCT/JP2016/088103.

*Primary Examiner* — Rowina J Cattungal
(74) *Attorney, Agent, or Firm* — Scully, Scott, Murphy & Presser, P.C.

(57) ABSTRACT

An endoscope device includes a main body part; a first insertion part having a tubular shape and including a first image sensor, and a first video signal transmission device converting a video output signal into an optical signal, optically transmitting the optical signal to a first proximal end part, and outputting a first video signal to the main body part; and a connector part configured to electrically couple the main body part with the first insertion part, including a main body part connector, and a first insertion part connector, wherein the first video signal is transmitted from the first insertion part to the main body part when the main body part connector is electrically coupled with the first insertion part connector, the first video signal transmission device includes a first photoelectrical converter at the first proximal end part, and the connector part is configured by an electrical connector.

5 Claims, 12 Drawing Sheets

(51) Int. Cl.
   *G02B 23/24*     (2006.01)
   *A61B 1/06*      (2006.01)
   *G02B 23/26*     (2006.01)
   *A61B 1/045*     (2006.01)
   *A61B 1/05*      (2006.01)
   *H04N 5/225*     (2006.01)

(52) U.S. Cl.
   CPC ...... *A61B 1/00013* (2013.01); *A61B 1/00114* (2013.01); *A61B 1/00124* (2013.01); *A61B 1/045* (2013.01); *A61B 1/05* (2013.01); *A61B 1/0676* (2013.01); *G02B 23/2423* (2013.01); *G02B 23/2446* (2013.01); *G02B 23/2476* (2013.01); *G02B 23/26* (2013.01); *H04N 5/37457* (2013.01); *H04N 2005/2255* (2013.01)

(56) References Cited

FOREIGN PATENT DOCUMENTS

| JP | 2015-000173 A |   | 1/2015  |              |
|----|---------------|---|---------|--------------|
| JP | 2015000173 A  | * | 1/2015  | ...... A61B 1/00013 |
| JP | 2015-173738 A |   | 10/2015 |              |
| JP | 2015173738 A  | * | 10/2015 |              |

\* cited by examiner

ENDOSCOPE DEVICE AND ENDOSCOPE SYSTEM

This application is a continuation application based on a PCT International Application No. PCT/JP2016/088103, filed on Dec. 21, 2016, whose priority is claimed on a Japanese Patent Application No. 2016-003610, filed on Jan. 12, 2016. The contents of both the PCT International Application and the Japanese Patent Application are incorporated herein by reference.

BACKGROUND OF THE INVENTION

Field of the Invention

The present invention relates to an endoscope device and an endoscope system.

In the industrial field and the medical field, an endoscope device is broadly used.

For example, an industrial endoscope is used for observing and inspecting crack and corrosion inside a subject such as a boiler, a turbine, an engine, and a chemical plant. For example, a medical endoscope is used for observing the organs inside the body cavity by inserting an elongated insertion part into the body cavity. The medical endoscope is also used to perform various treatments using treatment tools inserted through corresponding treatment tool channels of the medical endoscope as necessary.

The necessary insertion length of such an endoscope device varies corresponding to the different inspection target objects. Particularly, the necessary insertion length for the industrial endoscope covers a wide range from 1 meter to 30 meters, corresponding to the different inspection target subject. Preparation of various endoscope devices corresponding to various necessary insertion lengths in advance leads to a cost increase of the inspection.

Accordingly, an endoscope device configured to be attached with exchangeable different insertion part is proposed.

For example, in Japanese Unexamined Patent Application, First Publication No. 2006-116131, a medical endoscope device having an endoscope main body formed by an insertion part inserted into the body cavity and an operation part configured to operate the insertion part is disclosed. The insertion part has an interior body provided with a connection part at a proximal end side. The operation part has a connection part of an interior body thereof, wherein a diameter of the interior body of the operation part is larger than that of the interior body of the insertion part, and the connection part of the interior body of the insertion part is attachable to and detachable from the connection part of the interior body of the operation part. The main body of the endoscope device is configured to be able to change different insertion parts having different channel diameters and different numbers of signal lines. An optical transmission path of the insertion part is formed from an optical transmission light-guide fiber used for transmitting the illumination light.

SUMMARY OF THE INVENTION

According to a first aspect of the present invention, an endoscope device includes a main body part; a first insertion part having a tubular shape, the first insertion part including: a first image sensor disposed at a first distal end part in a distal side along a longitudinal direction of the endoscope device, and a first video signal transmission device, the first video signal transmission device configured to convert a video output signal from the first image sensor into an optical signal at the first distal end part, optically transmit the optical signal to a first proximal end part along the longitudinal direction, and output a first video signal to the main body part, the first video signal being a first video electrical signal generated by performing photoelectrical conversion with respect to the optical signal; and a connector part configured to electrically couple the main body part with the first insertion part, the connector part including: a main body part connector disposed at the main body part, and a first insertion part connector disposed at a proximal end of the first insertion part, the first insertion part connector being attachable to and detachable from the main body part connector, wherein the first video signal is transmitted from the first insertion part to the main body part when the main body part connector is electrically coupled with the first insertion part connector, wherein the first video signal transmission device includes a first photoelectrical converter at the first proximal end part, the first photoelectrical converter configured to perform photoelectrical conversion with respect to the optical signal to generate the first video electrical signal, and wherein the connector part is configured by an electrical connector for transmitting the first video electrical signal generated by the first photoelectrical converter to the main body part.

According to a second aspect of the present invention, in the endoscope device according to the first aspect, the first video signal transmission device may further include a first amplifier at the first proximal end part, the first amplifier configured to amplify the first video electrical signal.

According to a third aspect of the present invention, in the endoscope device according to the second aspect, the first video signal transmission device may further include a first A/D converter at the first proximal end part, the first A/D converter configured to perform A/D conversion with respect to the amplified first video electrical signal that is amplified by the first amplifier.

According to a fourth aspect of the present invention, in the endoscope device according to the first aspect, the first insertion part may further include a first non-video electrical signal transmission device, the first non-video electrical signal transmission device configured to metallically transmit a first non-video electrical signal from the first proximal end part to the first image sensor, and the first non-video electrical signal being transmitted from the main body part and including a control signal of the first image sensor, and the connector part may be configured to transmit the first non-video electrical signal from the main body part to the first insertion part, when the first insertion part connector is electrically coupled with the main body part connector.

According to a fifth aspect of the present invention, in the endoscope device according to the first aspect, the endoscope device may further include a second insertion part having a tubular shape, the second insertion part including: a second image sensor disposed at a second distal end part in the distal side along the longitudinal direction of the endoscope device; and a second video signal transmission device, the second video signal transmission device configured to metallically transmit a video output signal from the second image sensor to the second proximal end part along the longitudinal direction as a second video signal; wherein a second insertion part connector is disposed at the second insertion part, wherein the second insertion part connector is attachable to and detachable from the main body part connector, and wherein the second video signal is transmitted from the second insertion part to the main body part when the second insertion part connector is connected with the main body part connector.

According to a sixth aspect of the present invention, in the endoscope device according to the fifth aspect, a number of connection terminals included in the first insertion part connector may be the same with a number of connection terminals included in the second insertion part connector, and a signal arrangement at the connection terminals at the first insertion part connector may be the same with a signal arrangement at the connection terminals at the second insertion part connector.

According to a seventh aspect of the present invention, an endoscope system includes a main body part; a first insertion part having a tubular shape, the first insertion part including: a first image sensor disposed at a first distal end part in a distal side along a longitudinal direction of the endoscope device, and a first video signal transmission device, the first video signal transmission device configured to convert a video output signal from the first image sensor into an optical signal at the first distal end part, optically transmit the optical signal to a first proximal end part along the longitudinal direction, and output a first video signal to the main body part, the first video signal being a first video electrical signal generated by performing photoelectrical conversion with respect to the optical signal; a second insertion part having a tubular shape the second insertion part including: a second image sensor disposed at a second distal end part in the distal side along the longitudinal direction of the endoscope device, and a second video signal transmission device, the second video signal transmission device configured to metallically transmit a video output signal from the second image sensor to the second proximal end part along the longitudinal direction as a second video signal; a main body part connector disposed at the main body part; a first insertion part connector disposed at a proximal end of the first insertion part, the first insertion part connector being attachable to and detachable from the main body part connector, and the first video signal being transmitted from the first insertion part to the main body part when the first insertion part connector is electrically coupled with the main body part connector; and a second insertion part connector disposed at a proximal end of the second insertion part, the second video signal being transmitted from the second insertion part to the main body part when the second insertion part connector is electrically coupled with the main body part connector; wherein the first insertion part or the second insertion part is attachable to and detachable from the main body part.

According to an eighth aspect of the present invention, in the endoscope system according to the seventh aspect, the first video signal transmission device may include a first photoelectrical converter at the first proximal end part, the first photoelectrical converter configured to perform photoelectrical conversion with respect to the optical signal to generate the first video electrical signal, and the main body part connector may be configured by an electrical connector for transmitting the first video electrical signal generated by the first photoelectrical converter to the main body part.

According to a ninth aspect of the present invention, in the endoscope system according to the eighth aspect, the first video signal transmission device may further include an amplifier at the first proximal end part, the first amplifier configured to amplify the first video electrical signal.

According to a tenth aspect of the present invention, in the endoscope system according to the ninth aspect, the first video signal transmission device may further include a first A/D converter at the first proximal end part, the first A/D converter configured to perform A/D conversion with respect to the amplified first video electrical signal that is amplified by the first amplifier.

According to an eleventh aspect of the present invention, in the endoscope system according to the seventh aspect, the first insertion part may further include a first non-video electrical signal transmission device, the first non-video electrical signal transmission device configured to metallically transmit a first non-video electrical signal from the first proximal end part to the first image sensor, and the first non-video electrical signal being transmitted from the main body part and including a control signal of the first image sensor, and the connector part may be configured to transmit the first non-video electrical signal from the main body part to the first insertion part, when the first insertion part connector is electrically coupled with the main body part connector.

According to a twelfth aspect of the present invention, in the endoscope system according to the seventh aspect, a number of connection terminals included in the first insertion part connector may be the same with a number of connection terminals included in the second insertion part connector, and a signal arrangement at the connection terminals at the first insertion part connector may be the same with a signal arrangement at the connection terminals at the second insertion part connector.

DETAILED DESCRIPTION OF THE INVENTION

Embodiments of the present invention will be described by referring to the enclosed figures. In all of the enclosed figures, the same members or equivalent members will be labeled with the same numerals and a common description will be omitted even if they correspond to different embodiments.

First Embodiment

An endoscope device and an endoscope system according to a first embodiment of the present invention will be described.

Figure 1:
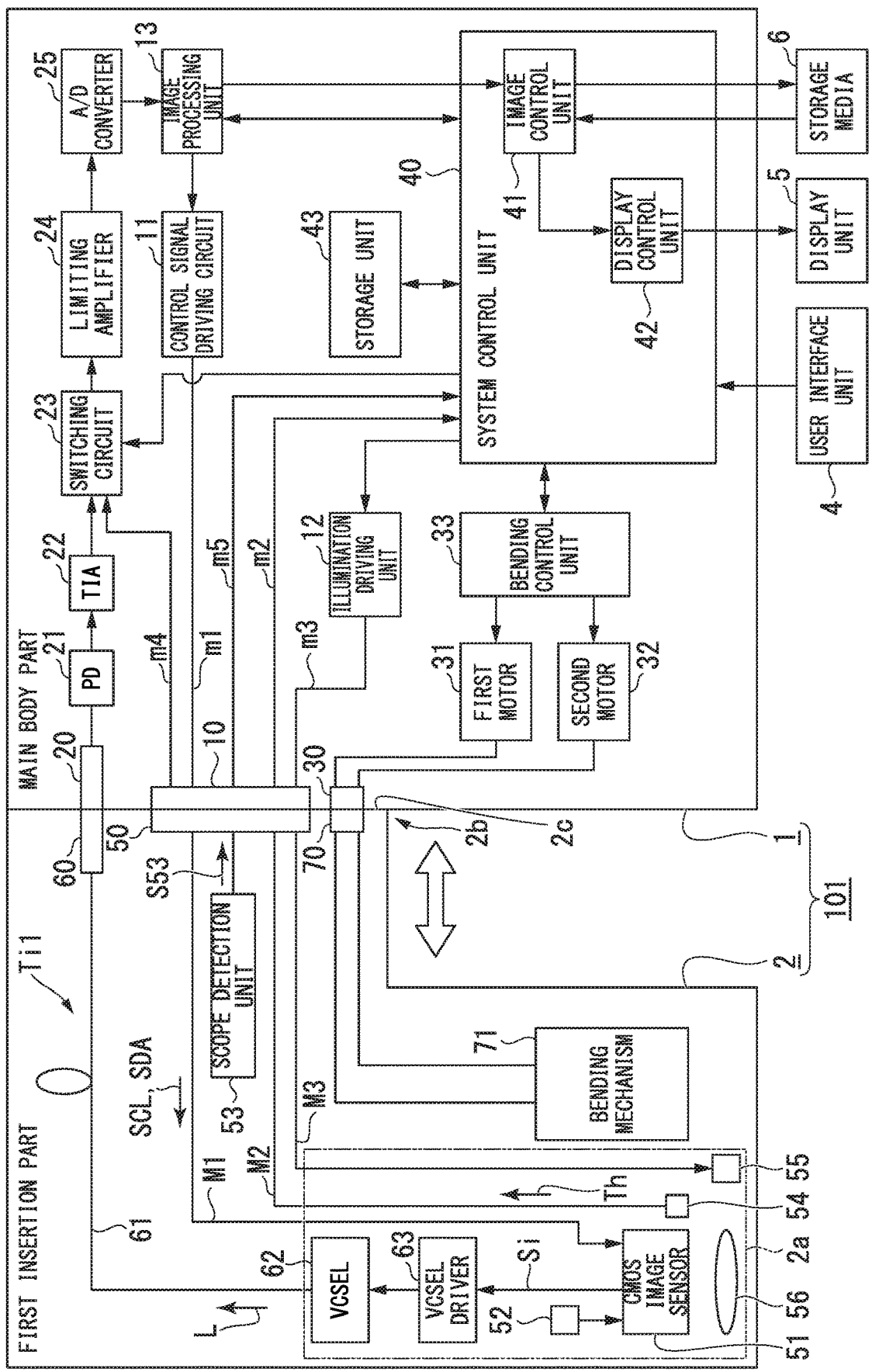
FIG. 1 is a block diagram showing a configuration example of an endoscope device according to a first embodiment of the present invention.
Figure 2:
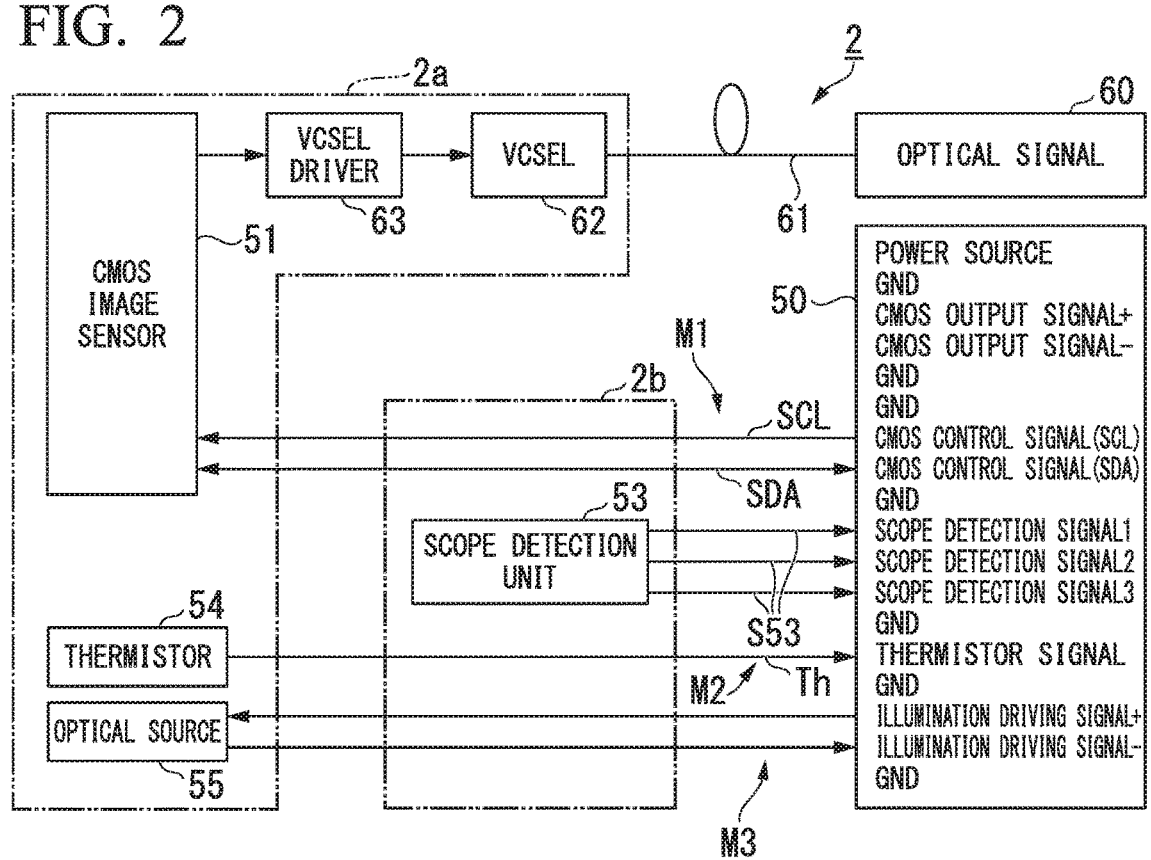
FIG. 2 is a schematic view showing a signal arrangement example of a first insertion part connector of the endoscope device according to the first embodiment of the present invention.
Figure 3:
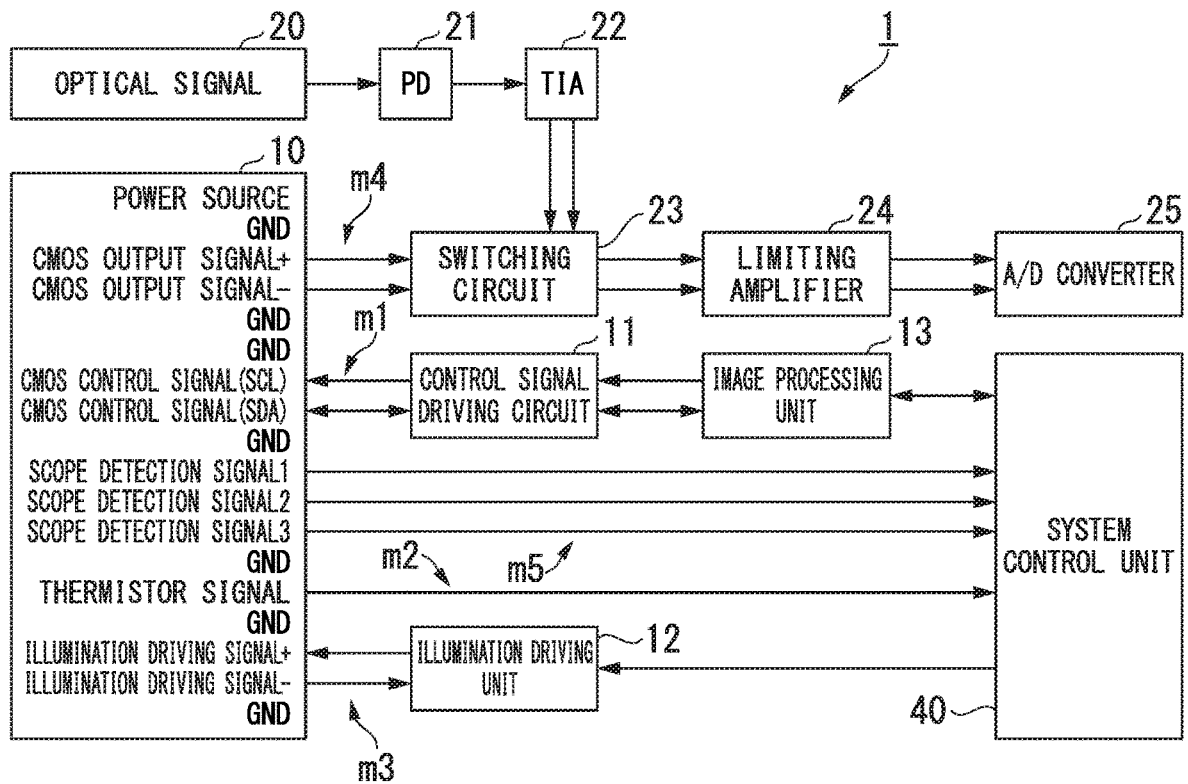
FIG. 3 is a schematic view showing a signal arrangement example of a main body connector of the endoscope device according to the first embodiment of the present invention.

FIG. 1 is a block diagram showing a configuration example of the endoscope device according to the first embodiment of the present invention. FIG. 2 is a schematic view showing a signal arrangement example of a first insertion part connector of the endoscope device according to the first embodiment of the present invention. FIG. 3 is a schematic view showing a signal arrangement example of a main body connector of the endoscope device according to the first embodiment of the present invention.

As shown in FIG. 1, an endoscope device 101 according to the present embodiment includes a first insertion part 2 and a main body part 1. The endoscope device 101 is inserted into the inside of a subject. The endoscope device 101 at least acquires a video image of the inside of the subject. Types of the subject are not limited thereto. For example, the subject as an inspection target of the endoscope device 101 can be an industrial apparatus such as a boiler, a turbine, an engine, and a chemical plant, and can be an organism.

The first insertion part 2 is a part of the endoscope device 101 configured to be inserted into the subject. The first insertion part 2 is bendable and has an elongated tubular shape. A length of the first insertion part 2 can be determined to be a suitable length corresponding to a distance from an opening of the subject to an inspection position inside the subject. In the present embodiment, as an example, the length of the first insertion portion 2 is approximately 30 meters.

A distal end part 2a (first distal part) is disposed at a distal end thereof along an insertion direction of the first insertion part 2.

At the distal end part 2a, an object lens 56, a CMOS image sensor 51 (first image sensor), an oscillator 52, a VCSEL 62, a VCSEL (Vertical Cavity Surface Emitting Laser) drive 63, an illumination light source 55, and a thermistor 54 are provided.

Even if now shown in FIG. 1, in order to allow the light from the subject to be incident, a light-transmissive light receiving window, and an illumination window configured to emit the light from the illumination light source 55 that will be described later are also provided at the distal end part 2a.

The object lens 56 is configured to image the light incident to the distal end part 2a and form an image on an image surface. The object lens 56 is configured to be opposite to the light receiving window disposed at the distal end part 2a that is not shown.

The CMOS image sensor 51 is configured to perform photoelectrical conversion with respect to the light from the subject. An imaging surface of the CMOS image sensor 51 is disposed on the image surface of the object lens 56.

The CMOS image sensor 51 is configured to perform photoelectrical conversion with respect to the received light based on a CMOS control signal output from the main body part 1 to generate and output an image output signal Si as a differential signal.

A number of the CMOS control signal varies due to the type of the CMOS image sensor 51. As shown in FIG. 1, as an example, CMOS control signal SCL (Serial Clock) and SDA (Serial Date) (first non-video electrical signal) are shown. The number of the CMOS control signal can be equal to or more than three.

The CMOS control signal SCL and SDA is generated at the main body part 1 that will be described later, and metallically transmitted to the CMOS image sensor 51 via a connecting cable M1 (first signal transmission unit) connected to the CMOS image sensor 51. It is noted that in the present description, the phrase "metallically transmit" refers to a transmission via a metal wire, a metal medium or the like rather than an optical transmission.

The oscillator 52 is configured to provide a driving clock to the CMOS image sensor 51. For example, the oscillator 52 can be configured as a crystal oscillator.

The VCSEL driver 63 is configured to convert the differential signal output from the CMOS image sensor 51 into a driving signal for driving the VCSEL 62 that will be described later.

The VCSEL 62 is configured to emit laser light as an optical signal L, wherein the laser light is modulated based on the control signal output from the VCSEL driver 63. The optical signal L output from the VCSEL 62 is optically coupled to a distal end of an optical fiber 61 (first image signal transmission unit), wherein the optical fiber 61 extends from the distal end part 2a to a proximal end part (first proximal end part) of the first insertion part 2.

A proximal end of the optical fiber 61 is connected to a first insertion part optical connector 60 (first insertion part connector, connecting unit) which is disposed at a proximal end 2c of the first insertion part 2.

The illumination light source 55 is configured to generate illumination light for illuminating the inside of the subject based on a driving signal output from the main body part 1. The illumination light generated by the illumination light source 55 is emitted outside of the distal end part 2a through the illumination window (not shown) of the distal end part 2a.

For example, the illumination light source 55 can be implemented by LED.

The driving signal to the illumination light source 55 is generated at the main body 1 that will be described later. The driving signal to the illumination light source 55 is metallically transmitted to the illumination light source 55 through a connecting cable M3.

The thermistor 54 is a temperature sensor configured to detect a temperature inside the distal end part 2a. A thermistor signal Th indicating the temperature detected by the thermistor 54 is metallically transmitted to the main body part 1 through the connecting cable M2.

The connecting cables M1, M2, M3 are inserted through the inside of the first insertion part 2 along the direction from the distal end part 2a toward the proximal end part 2b. Proximal ends of the connecting cables M1, M2, M3 are electrically connected to a first insertion part electrical connector 50 (first insertion part connector, connecting unit).

For example, the connecting cables M1, M2, M3 can be implemented by coaxial composite cables.

A scope detection unit 53 is disposed at the proximal end part 2b of the first insertion part 2.

The scope detection unit 53 is configured to generate a scope detection signal S53. The scope detection signal S53 is generated for informing the type of the first insertion part 2 to the main body part 1. A signal line of the scope detection unit 53 is wired to the first insertion part electrical connector 50.

In the present embodiment, the scope detection signal S53 can at least transmit the information indicating that the image output signal Si is optically transmitted as the optical signal L. Moreover, the scope detection signal S53 can transmit detectable information such as the length of the first insertion part 2, the type of the first insertion part 2, and the like. In the present embodiment, the scope detection signal S53 includes information regarding the length of the coaxial composite cable between the CMOS image sensor 51 and the proximal end part 2b, or information regarding the length of the first insertion part 2 (length of non-video electrical signal transmission path) corresponding to the length of the coaxial composite cable.

Here, the information regarding the length of non-video electrical signal transmission path may not be the length itself.

For example, in a situation when a lineup of the lengths of the insertion parts that can be attached to the main body part 1 to configure the endoscope device are limited to different n lengths (however, n is an integer equal to or more than 2), the information may be used to specify each of the lengths in stages such as a first length, . . . , a nth length.

Moreover, in a situation when the types of the first insertion part 2 are specified by predetermined identification numbers corresponding to the lengths of non-video electrical signal transmission paths in one to one correspondence, the identification numbers indirectly show the information corresponding to the lengths of the non-video electrical signal transmission paths.

For example, specific values of the lengths of the non-video electrical signal transmission paths corresponding to each information can be stored in a storage unit 43. In the present embodiment, as described below, the information corresponding to the lengths of the non-video electrical transmission paths is used as a parameter of the driving processing of a control signal driving circuit 11. Accordingly, the information corresponding to the lengths of the non-video electrical signal transmission paths may correspond to the parameters in one to one correspondence.

The signal generation means in the scope detection unit 53 is not limited thereto. The scope detection unit 53 may be configured to transmit the scope detection signal S53, and the scope detection unit 53 may be configured to retain the scope detection signal S53 such that the scope detection signal S53 can be read by the main body part 1. For example, the scope detection unit 53 may be configured to store the scope detection signal S53 as data in nonvolatile memory such as EEPROM (Electrically Erasable Programmable Read-Only Memory). In such a situation, during the connection with the main body part 1, the scope detection signal S53 stored in the nonvolatile memory as data can be read by the main body part 1.

An example of signal arrangement at the first insertion part electrical connector 50 will be described by referring to FIG. 2.

As shown in FIG. 2, for example, the first insertion part electrical connector 50 is a connector having 20 terminals. In the first insertion part electrical connector 50, except for the power source and GND terminals, signal lines are wired to 10 terminals thereof.

A [CMOS output signal +(−)] terminal is an input signal terminal for a signal corresponding to the differential signal of the image output signal Si by the CMOS image sensor 51. However, since the first insertion part 2 converts the image output signal Si to the optical signal L, the [CMOS output signal +(−)] terminal is not used during the connection with the first insertion part 2.

Both a [CMOS control signal (SCL)] terminal and a [CMOS control signal (SDA)] terminal are input and output signal terminals of the CMOS control signals SCL and SDA to the CMOS image sensor 51, respectively.

A [scope detection signal 1 (2, 3)] terminal is an output signal terminal of the 3-bit scope detection signal S53 output from the scope detection unit 53.

A [thermistor signal] terminal is an output signal terminal of the thermistor signal Th output from the thermistor 54.

A [illumination driving signal +(−)] terminal is a terminal used for transmitting the driving signal generated by the main body part 1 to the illumination light source 55.

As shown in FIG. 1, a bending mechanism 71 configured for changing the orientation of the distal end part 2a is disposed at the proximal end side of the distal end part 2a of the first insertion part 2.

Details of the bending mechanism 71 are not shown, and variable mechanisms used in the conventional endoscopes can be used.

For example, in the bending mechanism 71, four angle wires are inserted into bending pieces, wherein the bending pieces are connected with each other such that the bending pieces are alternatively tiltable in two axial directions orthogonal to a longitudinal direction of the first insertion part 2.

A distal end part of each angle wire is fixed to a wire fixing part of the distal end of the bending mechanism 71 (proximal end of the distal end part 2a). The angle wires are configured to be opposite to each other in the two axial directions corresponding to the tilting directions of the bending pieces, and the angle wires are extended to the proximal end part 2b through the inside of the first insertion part 2. Each of the angle wires is inserted through a coil sheath in the part of the first insertion portion 2 more proximal than the bending mechanism 71.

Each angle wire that is extended from the coil sheath and disposed in the proximal end part 2b is fixed to a wire connecting part 70 disposed at the proximal end 2c of the first insertion part 2.

The wire connecting part 70 can be attached to and detached from the wire connecting part 30 of the main body part 1. The wire connecting part 70 is configured to pull each of the angle wires along the longitudinal direction of the first insertion part 2 based on the driving amount of the wire connecting part 40 of the main body part 1 when the wire connecting part 70 is coupled to the wire connecting part 30.

The main body part 1 is disposed at outside of the subject.

The main body part 1 includes a main body part optical connector 20 (main body part connector, connecting part), a main body part electrical connector 10 (main body part connector, connecting part), and a wire connecting part 30 at an end part that is able to abut with the proximal end 2c of the first insertion part 2.

The main body part optical connector 20, the main body electrical connector 10, and the wire connecting part 30 are attachably and detachably connected with the first insertion part optical connector 60, the first insertion part electrical connector 50, and the wire connecting part 70, respectively.

In order to process the optical signal L output from the main body part optical connector 20, the main body part 1 further includes a photodiode (PD) 21, a transimpedance amplifier (TIA) 22, a switching circuit 23, a limiting amplifier 24, and an A/D conversion unit (converter) 25.

The PD 21 is a photoelectrical conversion element configured to perform photoelectrical conversion with respect to the optical signal L input to the main body part optical connector 20.

The TIA 22 is configured to perform current-voltage conversion with respect to the output current from the PD 21. A voltage signal corresponding to the optical signal L that is generated by the TIA 22 is transmitted to the switching circuit 23.

The switching circuit 23 includes a first input port connected to the TIA 22 and a second input port connected to a wiring m4 from the main body part electrical connector 10. The switching circuit 23 is configured to selectively switch between the signals input from the first input port and the second input port, based on a control signal from the system control unit 40, and output the selected signal to the output port.

The limiting amplifier 24 is configured to amplify the signal output from the switching circuit 23 with a flat high gain for each frequency such that an eye pattern opens. The signal amplified by the limiting amplifier 24 is output to the A/D conversion unit 25.

The A/D conversion unit 25 is configured to perform A/D conversion with respect to the signal output from the limiting amplifier 24 to generate digital data. The digital data generated by the A/D conversion unit 25 is output to an image processing unit 13 that will be described later.

The main body part 1 further includes the image processing unit 13, a control signal driving circuit 11, and an illumination driving unit 12.

The image processing unit 13 is connected to the system control unit 40 and the control signal driving circuit 11 and is able to communicate with the system control unit 40 and the control signal driving circuit 11. The image processing unit 13 performs both of driving control of the CMOS image sensor 51 and image processing of the digital data output from the A/D conversion unit 25, based on the control signal from the system control unit 40.

The image processing unit 13 is configured to output a control signal to the control signal driving circuit 11 for initiating the driving control of the CMOS image sensor 51 by the control signal driving circuit 11, when the system control unit 40 outputs the control signal instructing to start the imaging.

The control signal driving circuit 11 is electrically connected with the main body part electrical connector 10 via the wiring m1.

The control signal driving circuit 11 is configured to communicate with the CMOS image sensor 51 via the main body part electrical connector 10 and the first insertion part electrical connector 50. The control signal driving circuit 11 is configured to output the CMOS control signal SCL, SDA to the CMOS image sensor 51.

At this time, the control signal driving circuit 11 performs driving processing corresponding to the length of the non-video electrical signal transmission path with respect to the CMOS control signal SCL, SDA. Accordingly, the CMOS control signal SCL, SDA is generated having a signal strength corresponding to the length of the non-video electrical signal transmission path in response to the type of the first insertion part 2. A switching instruction for switching the information regarding the length of the non-video electrical signal transmission path and the corresponding driving processing is given by the control signal from the system control unit 40.

The image processing to the digital data that is performed by the image processing unit 13 includes the conventional signal processing in the imaging device, for example, such as white balance adjusting, gamma correction, contour correction, electrical zoom adjusting, color correction, contrast correction, and AE (automatic exposure) control.

The video signal after the image processing is output to the image control unit 41 of the system control unit 40.

The illumination driving unit 12 is connected to the system control unit 40 to be able to communicate with the system control unit 40. The illumination driving unit 12 is configured to generate driving signal for the illumination light source 55 based on the control signal from the system control unit 40. The illumination driving unit 12 is configured to control light on and light off of the illumination light source 55 based on the generated driving signal. In a situation when a luminance of the illumination light source 55 can be adjusted, the illumination driving unit 12 may also control the luminance of the illumination light source 55.

The driving signal generated by the illumination driving unit 12 is output to the main body part electrical connector 10 via the wiring m3.

An example of signal arrangement at the main body part electrical connector 10 will be described by referring to FIG. 3.

As shown in FIG. 3, the main body part electrical connector 10 has the same terminals as that of the first insertion part electrical connector 50. The main body part electrical connector 10 is an electrical connector having the terminals that can electrically connect with the terminals of the first insertion part electrical connector 50 in one to one correspondence.

A [CMOS output signal +(−)] terminal is wired to the first input port of the switching circuit 23 via the wiring m4.

A [CMOS control signal (SCL)] terminal and a [CMOS control signal (SDA)] terminal are wired to the control signal driving circuit 11 via the wiring m1.

A [scope detection signal 1 (2, 3)] is wired to the system control unit 40 via the wiring m5.

A [thermistor signal] terminal is wired to the system control unit 40 via the wiring m2.

An [illumination driving signal +(−) signal] terminal is wired to the illumination driving unit 12 via the wiring m3.

As shown in FIG. 1, the main body part 1 further includes a bending control unit 33, a first motor 31, and a second motor 32.

The bending control unit 33 is connected to and can communicate with the first motor 31, the second motor 32, and the system control unit 40. The bending control unit 33 is configured to control movement of the first motor 31 and the second motor 32 based on the control signal from the system control unit 40.

The first motor 31 and the second motor 32 are configured to be driven by the bending control unit 33 so as to pull the angle wires (not shown) connected to the wire connecting unit 30 and the wire connecting unit 70. Accordingly, the bending mechanism 71 can bend in the two axial directions in response to the pulling amount of the angle wires.

For example, the first motor 31 and the second motor 32 are connected to the angle wires performing up/down direction bending and left/right direction bending, respectively.

The main body part 1 further includes the system control unit 40 and a storage unit 43.

The system control unit 40 is configured to control the operation of whole endoscope device 101.

The system control unit 40 is not only connected to the above-described image processing unit 13, the main body part electrical connector 10, the illumination driving unit 12, and the bending control unit 33, but also connected to a user interface 4, the storage unit 43, a display unit 5, and a storage medium 6.

The user interface 4 is configured to include a suitable operation unit (not shown) such as a joy-stick, an operation switch, an operation button, and the like for an operator to perform operation input to the endoscope device 101. The user interface 4 is configured to output a control signal corresponding to the operation input via the operation unit to the system control unit 40.

The system control unit 40 is configured to control the operations of each part in response to the operation input via the user interface 4, when the first insertion part 2 or a second insertion part 202 is connected to the main body part 1.

The storage unit 43 is configured to be able to storage various parameters that are changed by the user operation such as the operation input via the user interface 4, the image processing parameters of the control of the image processing unit 13, and the control parameters regarding the bending of the bending mechanism 71. A relationship between the length of the non-video electrical signal transmission path and the parameters of the driving processing by the control signal driving circuit 11 is stored in the storage unit 43.

The system control unit 40 is configured to read the various parameters stored in the storage unit 43 as necessary.

The display unit 5 is configured to display various images based on the control signal from the system control unit 40. The images displayed by the display unit 5, for example, include the information necessary for the operation input and the like, the video image and the still image processed by the image processing unit 13, and the like.

The configuration of the display unit 5 is not limited thereto. For example, the display unit can be implemented by an LCD panel.

The storage medium 6 is configured to store the video image and the still image processed by the image processing unit 13 based on the control signal from the system control unit 40.

Examples of the operation control performed by the system control unit 40 are given as the light on and light off control of the illumination light source 55, the switching control of the switching circuit 23, the imaging control of the CMOS image sensor 51, the storage control of the video data, the bending control of the bending mechanism 71, the temperature detection control, and the like.

The light on and light off control of the illumination light source 55 is performed in response to the light on and light off operation input via the user interface 4. When the light on (light off) operation is input via the user interface 4, the system control unit 40 transmits the control signal instructing light on (light off) to the illumination driving unit 12.

Furthermore, when the operation input instructing to start the imaging operation is made via the user interface 4, the system control unit 40 initiates the control of the imaging operation, and automatically transmits the control signal instructing light on to the illumination driving unit 12.

The switching control of the switching circuit 23 is performed immediately after the first insertion part 2 or the second insertion part 202 is attached to the main body part 1 and the power is turned on.

When the system control unit 40 detects the scope detection signal S53 of the scope detection unit 53, the system control unit 40 analyzes the scope detection signal S53 so as to detect a signal transmission style of the video output signal Si in the connection opponent of the main body part 1.

When the system control unit 40 detects that the video output signal Si is optically transmitted as the optical signal L in the similar manner as that of the first insertion part 2, the system control unit 40 transmits the control signal to the switching circuit 23 so as to switch the input port of the switching circuit 23 to the first input port.

When the system control unit 40 detects that the video output signal Si is metallically transmitted as the electrical signal in the similar manner as that of the second insertion part 202, the system control unit 40 transmits the control signal to the switching circuit 23 so as to switch the input port of the switching circuit to the second input port.

The imaging operation control of the CMOS image sensor 51 is performed by transmitting the control signal to the image processing unit 13 from the system control unit 40 based on the operation input via the user interface 4.

The operation input via the user interface 4, for example, can include start imaging operation, stop imaging operation, zoom, luminance adjusting operation, and the like.

The image processing unit 13 transmits the control signal corresponding to the operation input to the control signal driving circuit 11 so as to start the operation of the CMOS image sensor 51.

The image processing unit 13 starts to acquire the video data that is output from the output port of the switching circuit 23, amplified by the limiting amplifier 24, and A/D converted by the A/D conversion unit 25 among the video signals output from the CMOS image sensor 51.

The acquired video data is transmitted to the image control unit 41 of the system control unit 40.

The image control unit 41 of the system control unit 40 is configured to perform the display control of the video data output from the image processing unit 13 and the storage control of the video data.

The video data output from the image processing unit 13 is transmitted to the display control unit 42 by the image control unit 41.

The display control unit 42 is configured to perform necessary signal processing to the video data in order to display the video data on the display unit 5 and transmits the video data to the display unit 5. The signal processing by the display control unit includes gamma correction, scaling, RGB conversion, and the like corresponding to display characteristic and display specification of the display unit 5.

Storage control of the video data is performed in response to the operation input via the user interface 4. For example, image storage operation via the user interface 4 can include freeze operation, still image storage operation, and video storage operation.

The freeze operation is an operation to cause the display unit 5 to display the video being displayed by the display unit 5 as a still image.

The still image storage operation is an operation to acquire a frame image of the video signal as a still image and store the still image in the storage medium 6. The still image storage operation may be performed continuously after the freeze operation.

The video storage operation is an operation to cause the storage medium 6 to store the video data from recording start to recoding stop in response to recording start operation input and recording stop operation input via the user interface 4.

The bending control is performed based on an operation of a joystick included in the user interface 4, for example. When the joystick is operated, the system control unit 40 calculates bending amounts corresponding to the operation amounts in each bending direction by analyzing the operation amounts in the two directions of the joystick. The system control unit 40 transmits the information regarding the calculated bending amount to the bending control unit 33. The bending control unit 33 is configured to drive the first motor 31 and the second motor 32 so as to pull the wire corresponding to the received information regarding the bending amounts. Accordingly, the bending mechanism 71 is bent corresponding to the operation of the joy stick.

The temperature detection control is performed based on the thermistor signal Th received by the system control unit 40 via the wiring m2. The storage unit 43 is configured to store allowable temperature of the insertion part that can be attached to the main body part 1. When the system control unit 40 receives the thermistor signal Th, the system control unit 40 converts the thermistor signal Th to the temperature and controls the display unit 5 to display the temperature.

Furthermore, in a situation when the system control unit 40 detects that the detected temperature is near the predetermined allowable temperature or the detected temperature exceeds the allowable temperature, the system control unit 40 controls the display unit 5 to display a waning message.

The system control unit 40 is a computer formed from a CPU, a memory, an input/output interface, an external storage medium, and the like, and the system control unit 40 is configured to execute suitable control program to generate the various control signals.

An operation of the endoscope device 101 will be described with a focus on the signal transmission.

As shown in FIG. 1, in the endoscope device 101, the first insertion part 2 and the main body part 1 are connected with each other by connecting the first insertion part optical connector 60, the first insertion part electrical connector 50, and the wire connecting part 70 with the main body part optical connector 20, the main body part electrical connector 10, and the wire connecting part 30, respectively.

The system control unit 40 of the main body part 1 is configured to detect a type of the first insertion part 2 by detecting the scope detection signal S53 of the scope detection unit 53 at the first insertion part 2. Accordingly, the system control unit 40 can control the first insertion part 2 in accordance with the type thereof based on the various control parameters stored in the storage unit 43.

In the endoscope device 101, the system control unit 40 is configured to detect that the first insertion part 2 optically transmits the video output signal Si as the optical signal L due to the scope detection signal S53. Accordingly, the system control unit 40 switches the input port of the switching circuit 23 to the first input port.

When the operator performs operation input via the user interface 4, the system control unit 40 performs operation control in response to the operation input.

For example, when the operator performs the operation input of turning on the illumination light source 55 and starting imaging of the CMOS image sensor 51, the system control unit 40 transmits the control signal instructing light on of the illumination light source 55 and the control signal instructing starting imaging of the CMOS image sensor 51 to the illumination driving unit 12 and the image processing unit 13, respectively.

Accordingly, the illumination driving signal instructing light on is metallically transmitted from the illumination driving unit 12 to the illumination light source 55 via the wiring m3 and the connecting cable M3. The illumination driving signal has a remarkably lower frequency than that of the video output signal Si output from the CMOS image sensor 51 such that the illumination driving signal almost does not attenuate even if it is metallically transmitted for more than 30 meters.

The image processing unit 13 transmits the control signal to the control signal driving circuit 11 such that the CMOS control signal SCL, SDA for the imaging of the CMOS image sensor 51 is generated by the control signal driving circuit 11. The CMOS control signal SCL, SDA is metallically transmitted to the CMOS image sensor 51 via the wiring m1 and the connecting cable M1.

The CMOS control signal SLC, SDA has a lower frequency than that of the video output signal Si output from the CMOS image sensor 51 such that signal attenuation with respect to the CMOS control signal SLC, SDA is small. Particularly, in the present embodiment, the CMOS control signal SCL, SDA is processed by the driven processing according to the length of non-video electrical transmission path performed by the control signal driving circuit 11 such that an adequate signal level is maintained at the CMOS image sensor 51.

Furthermore, in the present embodiment, a driving clock of the CMOS image sensor 51 having a higher frequency than that of the CMOS control signal SCL, SDA, is provided from the oscillator 52 disposed at the distal end part 2a to the CMOS image sensor 51. Accordingly, the transmission distance of the driving clock is only a few millimeters. As a result, the driving clock is provided to the CMOS image sensor without any deterioration.

The thermistor signal Th is metallically transmitted from the thermistor 54 disposed at the first insertion part 2 to the main body part 1 via the first insertion part electrical connector 50 and the main body part electrical connector 10. The thermistor signal Th, for example, does not attenuate even if it is metallically transmitted more than 30 meters.

Since a plurality of image signal of each pixel is transmitted by serial communication, the higher the resolution is, the video output signal Si from the CMOS image sensor 51 becomes a signal having a higher frequency. Accordingly, for example, if the video output signal Si is metallically transmitted via a cable having a length equal to or more than 30 meters, it is concerned that the signal waveform will significantly deteriorate. Furthermore, during the process of metallically transmission, it is easy to pick up an external noise such that the S/N ratio deteriorates.

In the present embodiment, at the distal end part 2a, the VCSEL 62 and the VCSEL driver 63 are disposed in the vicinity of the CMOS image sensor 51. The video output signal Si is converted into the driving signal of the VCSEL 62 by the VCSEL driver 63. The VCSEL 62 generates laser and outputs the optical signal L in response to the driving signal from the VCSEL driver 63.

The optical signal L is optically coupled to the optical fiber 61 disposed opposite to the VCSEL 62 and the optical signal L is optically transmitted in the first insertion part 2 until the first insertion part optical connector 60 at the proximal end part 2b.

In the first insertion part 2, the video output signal Si is metallically transmitted in the distal end part 2a for only a few millimeters such that the video output signal Si is converted into the optical signal L almost without any deterioration.

Since the video output signal Si is optically transmitted as the optical signal L for almost the whole length of the inside of the first insertion part 2, for example in a situation that the length of the first insertion part is near 30 meters, the video output signal Si is transmitted almost without any deterioration. The optical signal L is optically transmitted so as to prevent the external noise being mixed.

The optical signal L reaching the first insertion part optical connector is optically coupled to the main body part optical connector 20 and input to the PD 21 inside the main body part 1.

The PD 21 performs photoelectric conversion with respect to the optical signal L and output a current signal to the TIA 22. The TIA 22 coverts the current signal generated by the photoelectric conversion to a voltage signal. The voltage signal converted by the TIA 22 is output to the limiting amplifier 24 through the first input port to the output port of the switching circuit 23.

The limiting amplifier 24 amplifies the signal output from the switching circuit 23 with a flat high gain for each frequency such that the eye pattern opens. Thus, even if the S/N ratio is reduced in the main body part 1, a signal with a high S/N ratio can be recovered.

The amplified signal by the limiting amplifier 24 is output to the A/D conversion unit 25.

The A/D conversion unit is configured to perform an A/D conversion with respect to the signal output from the limiting amplifier 24 so as to generate a more stable digital data. The digitalized video data by the A/D conversion unit 25 is output to the image processing unit 13.

The image processing unit 13 is configured to perform suitable image processing with respect to the video signal and output the video data to the image control unit 41 of the system control unit 40. The image control unit 41 is configured to output the video data to the display control unit 42. The display control unit 42 is configured to perform necessary signal processing with respect to the video data and control the display unit 5 to display the video data.

In such a manner, according to the endoscope device 101, the video data based on the video output signal Si captured by the CMOS image sensor 51 is displayed at the display unit 5 while the signal deterioration and external noise mixing due to the signal transmission paths in the first insertion part 2 and the main body part 1 are suppressed.

Accordingly, in the endoscope device 101, even if the video signal displaying a high-resolution video is transmitted through a transmission path having a length near 30 meters, a high-quality image of the video can be displayed.

The operator can perform the operation input via the user interface 4 such as the freeze operation, the still image storage operation, and the video storage operation while seeing the content displayed at the display unit 5.

Furthermore, the operator can perform zoom adjusting and luminance adjusting by performing operation input via the user interface 4 so as to display the video in a way easier to see.

Furthermore, the operator can operate the joystick of the user interface 4 to bend the bending mechanism 71 in appropriate directions so as to direct an optical axis of the object lens 56 to a suitable direction inside the subject.

As shown in FIG. 1, according to the present embodiment, a first video signal transmission unit Ti1 is configured by the VCSEL 62, the VCSEL driver 63, and the optical fiber 61, the first video signal transmission unit Ti1 is configured to convert the video output signal of the first image sensor to the optical signal at the first distal end part, optically transmit the optical signal to the first proximal end part along the insertion direction and output the first video signal generated from the optical signal.

In the endoscope device 101, according to the subject, the first insertion part 2 can be exchanged to other insertion part. For example, in a situation when a length of the insertion part may be shorter according to the position of the subject, the first insertion part 2 may be exchanged to an insertion part having a shorter length than that of the first insertion part 2.

Figure 4:
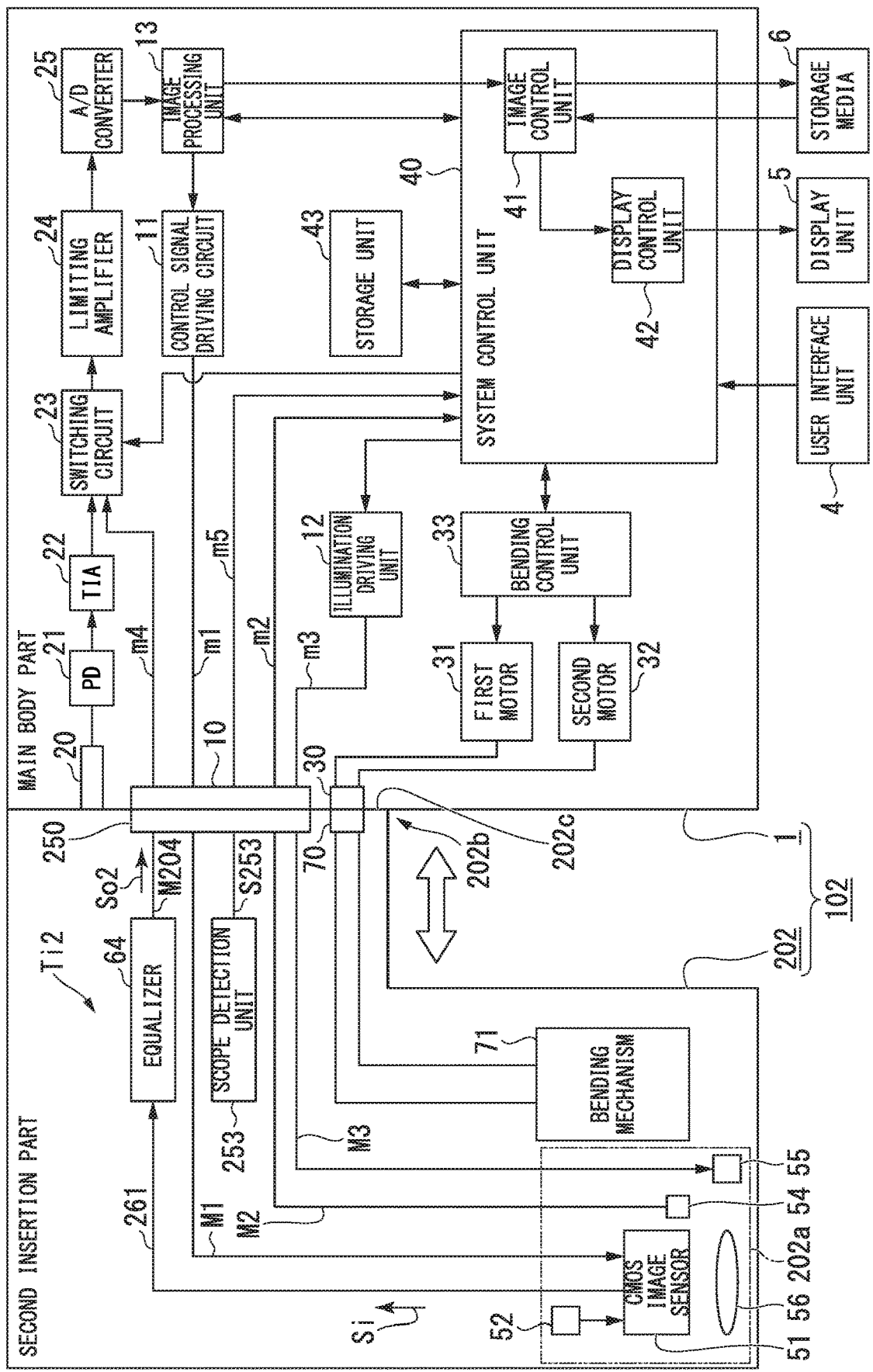
FIG. 4 is a block diagram showing a configuration example of attaching a second insertion part to the main body part of an endoscope system according to the first embodiment of the present invention.
Figure 5:
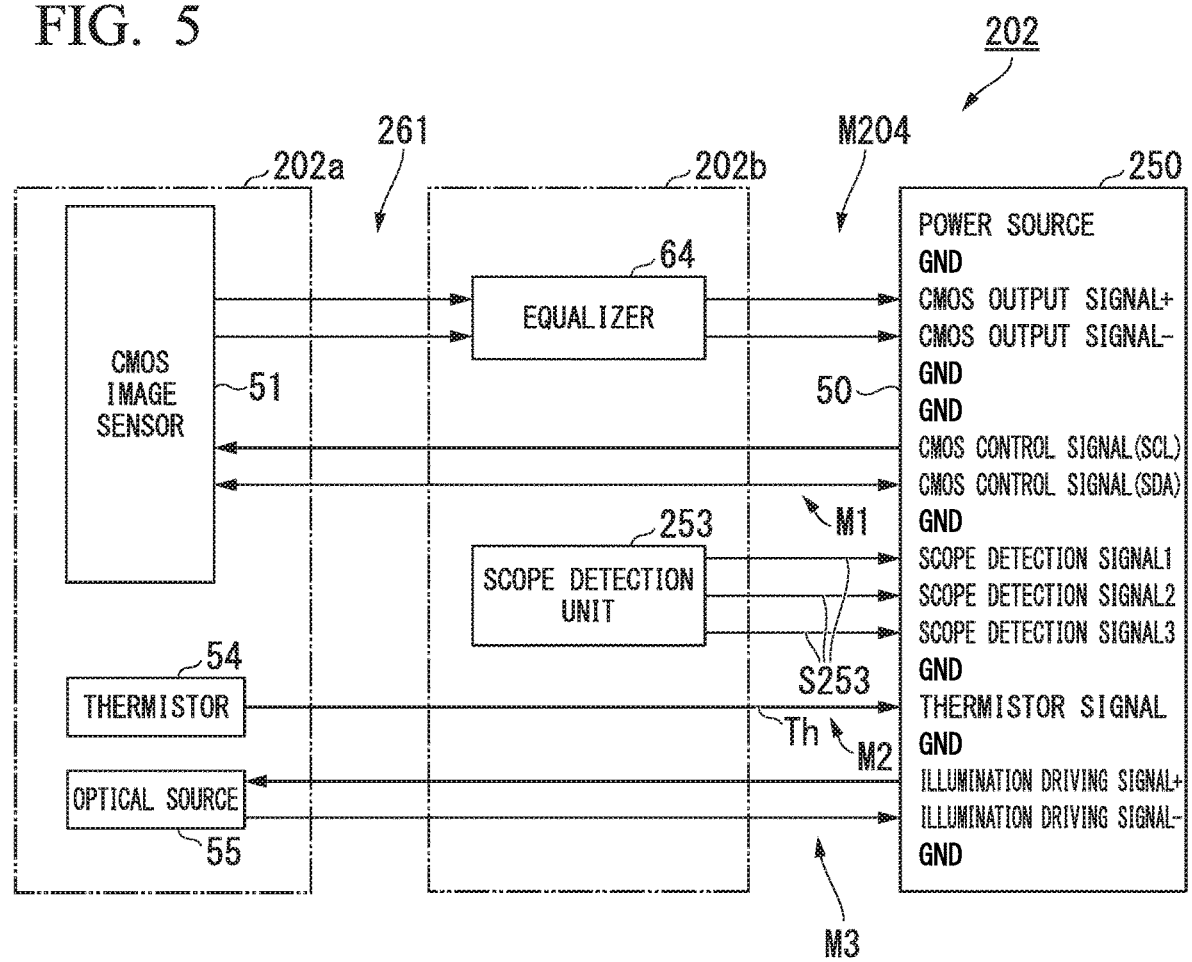
FIG. 5 is a schematic view showing a signal arrangement example of a second insertion part connector of the endoscope system according to the first embodiment of the present invention.

FIG. 4 is a block diagram showing a configuration example of attaching a second insertion part to the main body part of the endoscope system according to the first embodiment of the present invention. FIG. 5 is a schematic view showing a signal arrangement example at the second insertion part connector according to the first embodiment of the present invention.

As shown in FIG. 4, the endoscope device 102 includes a second insertion part 202 instead of the first insertion part 2 of the above-described endoscope device 101.

The length of the second insertion part 202 is shorter than that of the first insertion part 2. The second insertion part 202 is configured to metallically transmit the video output signal Si that will be described later. Accordingly, it is preferable that the length of the second insertion part 202 does not exceed 10 meters.

The second insertion part 202 is configured to include a distal end part 202a (second distal end part), a connecting cable 261 (second video signal transmission unit), and a proximal end part 202b (second proximal end part) instead of the above-described distal end part 2a of the first insertion part 2, the optical fiber 61, and the proximal end part 2b, respectively. The configurations in the distal end part 202a and the proximal end part 202b are partially different from that of the distal end part 2a and the proximal end part 2b, respectively.

The second insertion part 202 will be described with a focus on the differences from the first insertion part 2.

The distal end part 202a is configured by excluding the VCSEL 62 and the VCSEL driver 63 from the configuration of the distal end part 2a.

The connecting cable 261 is configured to metallically transmit the differential signal of the CMOS image sensor 51 (second image sensor) at the distal end part 202a as the video output signal Si to the proximal end part 202b. The connecting cable 261 is configured as a coaxial composite cable together with the connecting cable M1 (second signal transmission unit) and the connecting cables M2 and M3 at the distal end part 202a.

In the connecting cable M1, the CMOS control signal SCL, SDA (second non-video electrical signal) for controlling the CMOS image sensor 51 at the distal end part 202a is metallically transmitted.

The CMOS image sensor 51, the oscillator 52, and the object lens 56 at the distal end part 202a may have different configurations from that of the first insertion part 2. For example, the CMOS image sensor 51 at the distal end part 202a may have a lower resolution than that of the CMOS image sensor of the first insertion part 2. In this case, the oscillator 52 at the distal end part 202a may have a lower frequency than that of the oscillator 52 at the first insertion part 2. For example, the object lens 56 at the distal end part 202a may have a different angle of view than that of the object lens at the first insertion part 2.

An example of the distal end part 202a having the CMOS image sensor 51, the oscillator 52, and the object lens 56 with the same configuration as that of the first insertion part 2 will be described.

An internal configuration of the proximal end part 202b includes a second insertion part electrical connector 250 and a scope detection unit 253, instead of the first insertion part electrical connector 50 and the scope detection unit 53 disposed at the proximal end part 2b of the first insertion part 2. Furthermore, regarding the internal configuration of the proximal end part 202b, the first insertion part optical connector 60 is excluded and an equalizer 64 is added.

The second insertion part electrical connector 250 is the same electrical connector as the first insertion part electrical connector 50. However, as shown in FIG. 5, the second insertion part electrical connector 250 is different from the first insertion part electrical connector 50 in the respect that the second insertion part electrical connector 250 is wired to the [CMOS output signal +(−)] terminal via the wiring M204 (second video signal transmission unit).

The scope detection unit 253 is the part configured to generate the scope detection signal S253. The scope detection signal S253 is generated for informing the type of the second insertion part 202 to the main body part 1. The scope detection unit 253 has the same configuration as that of the scope detection unit 53, except for that the generated signal is different. The signal lines of the scope detection unit 253 are wired to the [ scope detection signal 1 (2, 3)] terminals of the second insertion part electrical connector 250.

The scope detection signal S253 at least includes information that the video output signal Si is metallically transmitted and information regarding the length of the metallically transmission path.

The equalizer 64 is configured to correct signal level of each frequency of the video output signal Si such that the signal level of each frequency becomes substantially the same, wherein the video output signal Si attenuates due to the transmission through the connecting cable 261. Based on the attenuation characteristic of the connecting cable 261, the equalizer 64 is configured to amplify the high-frequency component of the video output signal Si with a higher gain and amplify the low-frequency component of the video output signal Si with a lower gain such that the signal level of each frequency of the video output signal Si is corrected to be substantially the same.

A second video signal Sot (second video signal) that is corrected by the equalizer 64 is transmitted to the second insertion part electrical connector 250 via the wiring M204, wherein the second insertion part electrical connector 250 is disposed in the vicinity of the equalizer 64.

As the above description, the endoscope device 102 is different from the endoscope device 101 in the aspect that the video output signal Si is metallically transmitted by the connecting cable 261 (second video signal transmission unit).

Operations of the endoscope device 102 will be described with a focus on the difference from the endoscope device 101.

As shown in FIG. 4, in the second insertion part 202, the second insertion part 202 and the main body part 1 are connected with each other by connecting the second insertion part electrical connector 250 and the wire connecting part 70 to the main body electrical connector 10 and the wire connecting part 30, respectively.

The system control unit 40 of the main body part 1 is configured to detect the type of the second insertion part 202 by detecting the scope detection signal S253 from the scope detection unit 253 of the second insertion part 202. Accordingly, the system control unit 40 can control the second insertion part 202 in accordance with the type of the second insertion part 202 based on the various parameters stored in the storage unit 43.

The system control unit 40 is configured to detect that the second insertion part 202 metallically transmit the video output signal Si as an electrical signal by detecting the scope detection signal S253. Accordingly, the system control unit 40 controls switching the input port of the switching circuit 23 to the second input port.

In the endoscope device 102, the main body part optical connector 20, the PD 21, and the TIA 22 are not used.

A signal flow of the endoscope device 102 is almost the same with that of the endoscope device 101 except for that the signal output from the limiting amplifier 24 is the second video signal Sot that is metallically transmitted by the connecting cable 261 inside the second insertion part 202 and whose signal level is corrected by the equalizer 64.

However, the system control unit 40 is configured to detect that a length of the non-video electrical transmission path (the length of the coaxial composite cable including the connecting cable M1) in the second insertion part 202 is different from that of the first insertion part 2 and transmit a notice to the image processing unit 13. Accordingly, the image processing unit 13 is configured to control the control signal driving circuit 11 to perform driving processing based on the length of the non-video electrical transmission path of the second insertion part 202.

In the endoscope device 102, since the video output signal Si is metallically transmitted from the distal end part 202a to the proximal end part 202b through the connecting cable 261, signal attenuation and the deterioration of S/N ratio occur at the proximal end part 202b. However, the second insertion part 202 has the equalizer 64 at the proximal end part 202b such that the second video signal Sot output to the main body part 1 is corrected by the equalizer 64, particularly the signal attenuation of the high-frequency component is corrected. Accordingly, the second video signal Sot is recovered to the video data substantially the same with the original video output signal Si by the limiting amplifier 24 and the A/D conversion unit 25.

In this way, the endoscope device 102 can display a high-quality video even if the video output signal Si is metallically transmitted in the second insertion part 202.

Since the endoscope device 102 does not convert the video output signal Si to the optical signal L at the distal end part 202a, the internal configuration of the distal end part 202a is simplified and miniaturized.

The connecting cable 261 can be configured by the coaxial composite cable including the connecting cables M1, M2, M3. In the second insertion part 202, the optical fiber 61 is reduced such that an outer diameter of the second insertion part 202 is reduced.

As shown in FIG. 4, in the present embodiment, a second video signal transmission unit Ti2 is configured by the connecting cable 261, the equalizer 64 and the wiring M204, and the second video signal transmission unit Ti2 is configured to metallically transmit the video output signal of the second image sensor to the second proximal end part as the second video signal along the insertion direction.

As the above description, the main body part 1 used in the endoscope device 101 according to the present embodiment includes the main body part optical connector 20, the main body part electrical connector 10, and the switching circuit 23. The main body electrical connector 10 is connected to the first insertion part electrical connector 50 and the second insertion part electrical connector 250. The video output signal Si from the first insertion part 2 is converted in the first insertion part 2 and optically transmitted to the main body 1 via the main body optical connector 20. The video output signal Si from the second insertion part 202 is metallically transmitted to the main body part 1 via the second insertion part electrical connector 250 and the main body part electrical connector 10.

The main body part connectors including the main body part optical connector 20 and the main body part electrical connector 10, and the first insertion part connectors including the first insertion part optical connector 60 and the first insertion electrical connector 50 form a connector part configured to transmit the first video signal and the first non-video electrical signal when the main body part connectors and the first insertion part connectors are connected with each other.

Accordingly, the main body part 1 is free to exchange with the first insertion part 2 having the optical transmission path or the second insertion part 202 only having the metal transmission path. The main body part 1 can exchange the connection opponent with the first insertion part 2 and the second insertion part 202 as necessary to display the video of the subject and store the video of the subject.

The first insertion part 2, the second insertion part 202, and the main body part 1 according to the present embodiment can configure the endoscope device 101 and the endoscope device 102 by connecting the exchangeable first insertion part 2 and the second insertion part 202 with the main body part 1, and the first insertion part 2, the second insertion part 202, and the main body part 1 form an endoscope system according to the present embodiment.

Second Embodiment

An endoscope device and an endoscope system according to a second embodiment of the present invention will be described.

Figure 6:
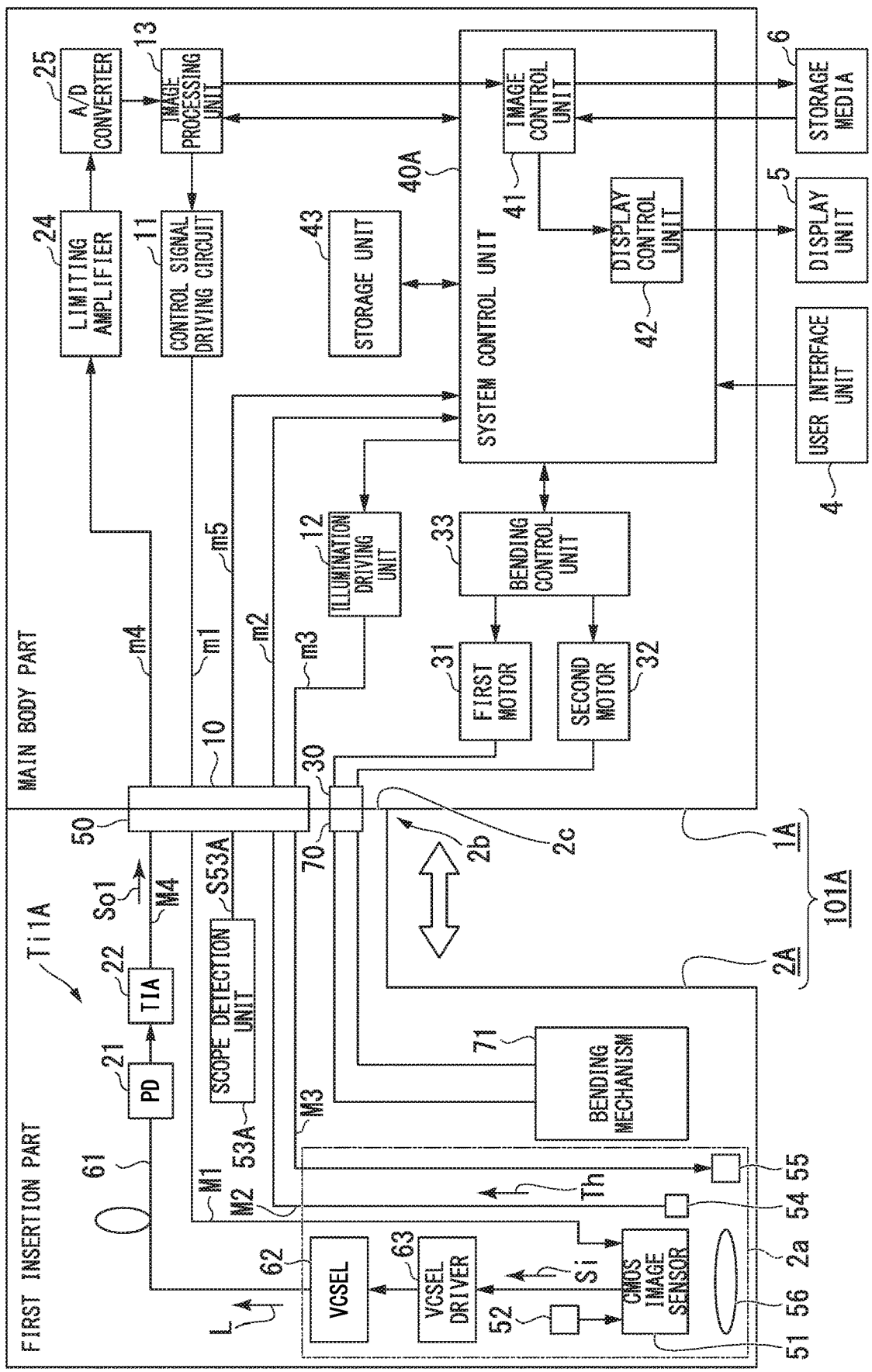
FIG. 6 is a block diagram showing a configuration example of an endoscope device according to a second embodiment of the present invention.
Figure 7:
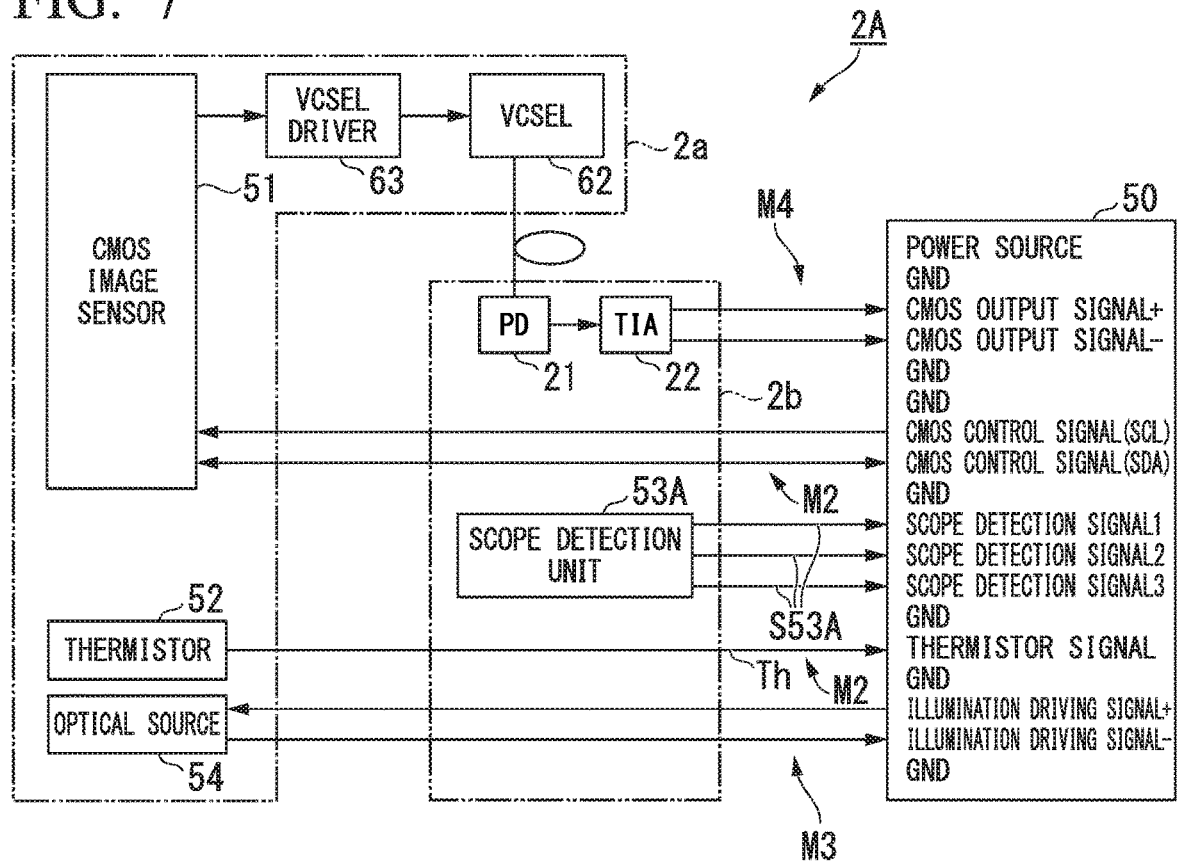
FIG. 7 is a schematic view showing a signal arrangement example of a main body connector of the endoscope device according to the second embodiment of the present invention.
Figure 8:
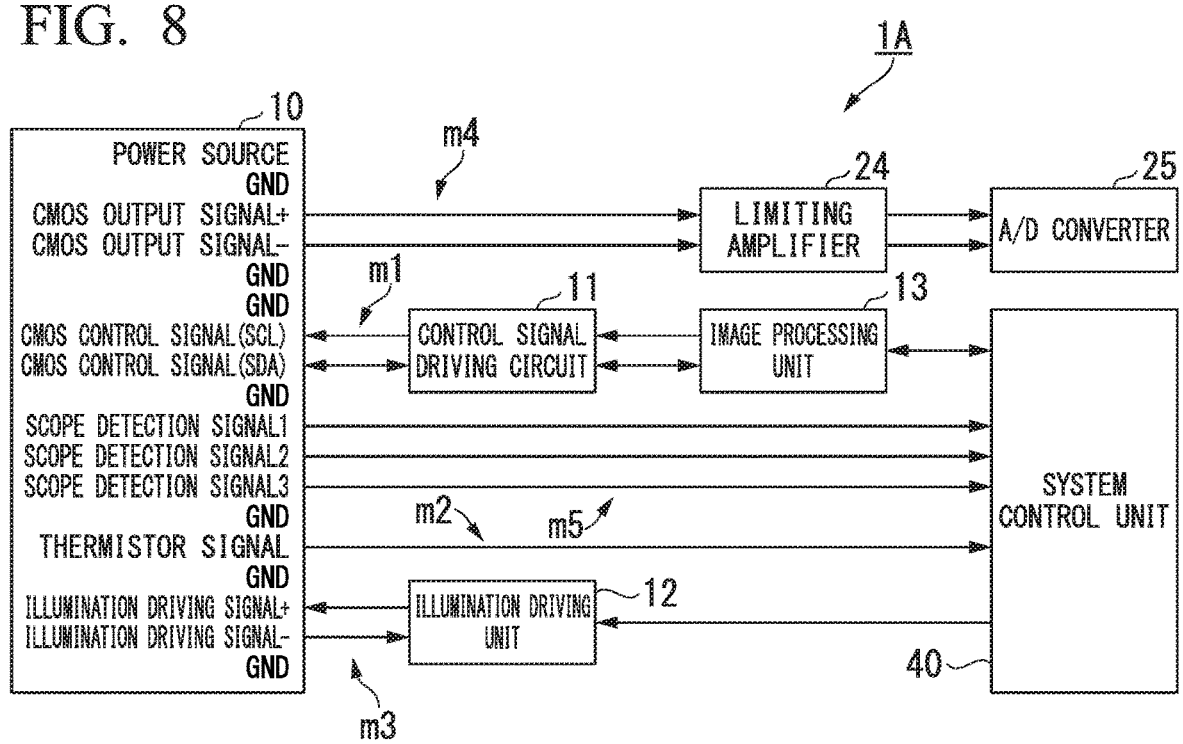
FIG. 8 is a schematic view showing a signal arrangement example of a first insertion part connector of the endoscope device according to the second embodiment of the present invention.
Figure 9:
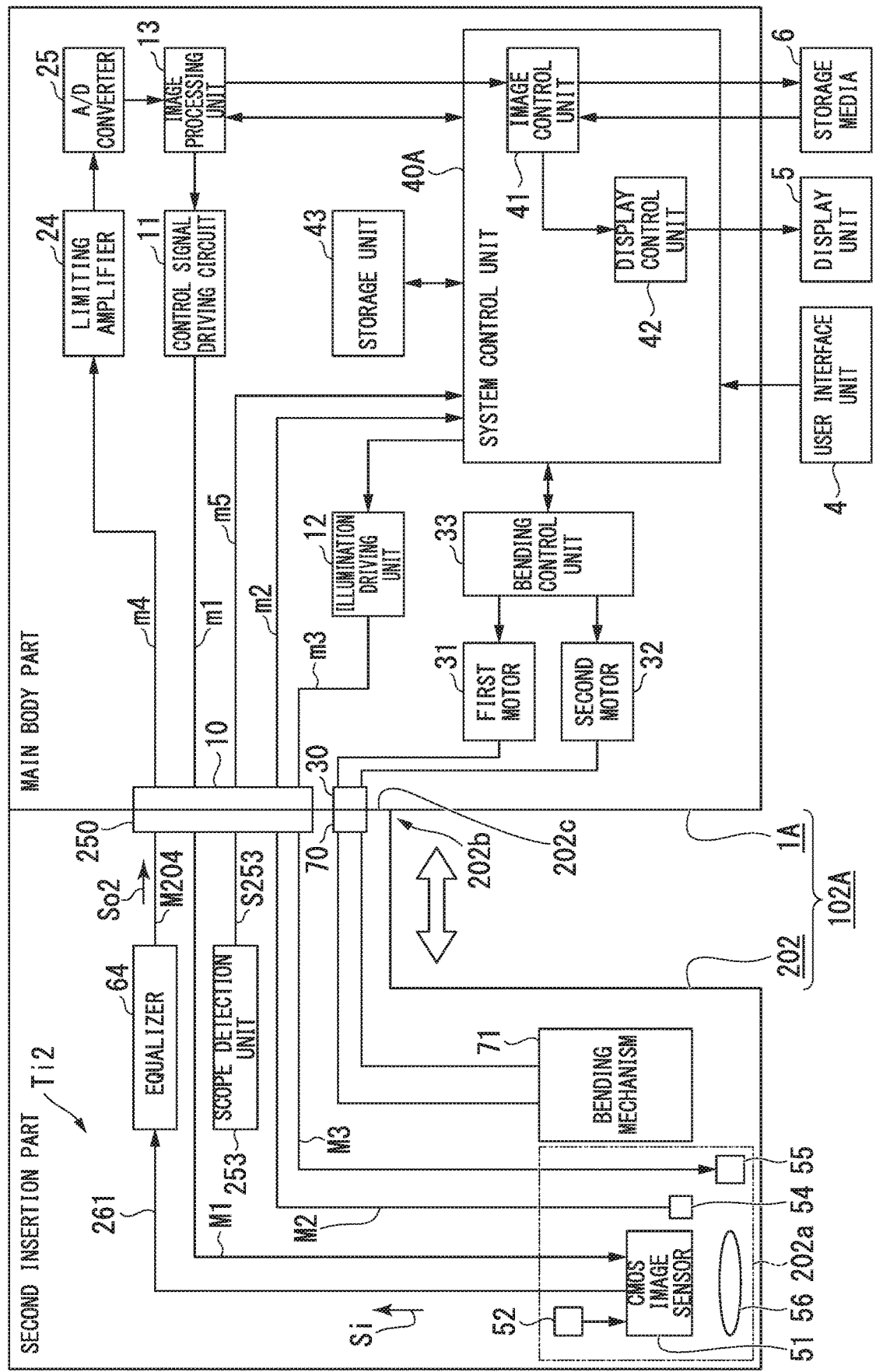
FIG. 9 is a block diagram showing a configuration example of attaching a second insertion part to the main body part of an endoscope system according to the second embodiment of the present invention.

FIG. 6 is a block diagram shows a configuration example of an endoscope device according to the second embodiment of the present invention. FIG. 7 is a schematic view showing a signal arrangement example at a first insertion part connector of the endoscope device according to the second embodiment of the present invention. FIG. 8 is a schematic view showing a signal arrangement example at a main body part connector of the endoscope device according to the second embodiment of the present invention. FIG. 9 is a block diagram showing a configuration example of attaching a second insertion part to the main body part of an endoscope system according to the second embodiment of the present invention.

As shown in FIG. 6, an endoscope device 101A according to the present embodiment includes a first insertion part 2A and a main body part 1A instead of the first insertion part 2 and the main body part 1 of the endoscope device 101 according to the above first embodiment, respectively.

The first insertion part 2A includes a scope detection unit 53A instead of the scope detection unit 53 at the first insertion part 2 according to the first embodiment, and the first insertion part 2A further includes the PD 21 and the TIA 22.

The main body 1A includes a system control unit 40A instead of the system control unit 40 at the main body part 1 according to the first embodiment, and the main body 1A is configured by excluding the main body optical connector 20, the PD 21, the TIA 22, and the switching circuit 23.

The configuration of the endoscope device 101A will be described with a focus on the difference from the first embodiment.

The scope detection unit 53A is configured to generate a scope detection signal S53A. The scope detection signal 53A is generated for informing the type of the first insertion part 2A to the main body part 1A. The scope detection unit 53A has the same configuration as that of the scope detection unit 53 according to the first embodiment except for that the generated signal is different. Signal lines of the scope detection unit 53A are wired to [scope detection signal 1 (2, 3)] terminals of the first insertion part electrical connector 50 (see FIG. 7).

The scope detection signal S53A at least includes information regarding the length of the non-video electrical signal transmission path at the first insertion part 2A.

The PD 21 according to the present embodiment is disposed at the proximal end part 2b of the first insertion part 2A. The PD 21 according to the present embodiment is configured to receive the optical signal L output from the proximal end part of the optical fiber 61 and perform photoelectrical conversion with respect to the optical signal L.

The TIA 22 according to the present embodiment is disposed at the proximal end part 2b of the first insertion part 2A. The TIA 22 according to the present embodiment is configured to perform a current/voltage conversion with respect to the output current of the PD 21.

As shown in FIG. 7, output terminals of the TIA 22 are connected to [CMOS output signal +(−)] terminals at the first insertion part electrical connector 50.

Accordingly, the voltage signal generated by the TIA 22 is metallically transmitted to the main body part 1A as a first video signal Sol (first video electrical signal, see FIG. 6) via the [CMOS output signal +(−)] terminals.

In the main body part 1A, the switching circuit 23 in the main body part 1 according to the first embodiment is exclude. Accordingly, as shown in FIG. 8, in the main body part 1A, [CMOS output signal +(−)] terminals of the main body part electrical connector 10 are wired to the limiting amplifier 24 via the wiring m4.

The system control unit 40A of the main body part 1A has the same configuration as that of the system control unit 40 according to the first embodiment except for the switching control of the switching circuit 23 is not performed.

The system control unit 40A does not perform the switching control of the switching circuit 23 such that the control program according to the present embodiment is simplified than that of the system control unit 40 according to the first embodiment.

In the endoscope device 101A, the PD 21 and the TIA 22 disposed between the main body part electrical connector 10 and the limiting amplifier 24 of the main body part 1 according to the first embodiment are moved to a position between the proximal end part of the optical fiber 61 and the first insertion part electrical connector 50 at the proximal end part 2*b* of the first insertion part 2A.

The movement amount of the PD 21 and the TIA 22 is extremely short compared to the length of the first insertion part 2A. Accordingly, a ratio of the metal transmission path to the transmission path of the video output signal Si and the first video signal Sol is extremely small compared to the optical transmission path, as the same as the first insertion part 2 according to the first embodiment.

On the other hand, the length of the non-video electrical signal transmission path at the first insertion part 2A is the same as the length of the non-video electrical signal transmission path according to the first embodiment.

As a result, in the endoscope device 101A, as the same as the endoscope device 101 according to the first embodiment, the video signal showing the video with a high-resolution can be displayed with a high-quality even if it is transmitted through a long transmission path such as 30 meters.

In the first insertion part 2A, the first insertion part optical connector 60 of the first insertion part 2 according to the first embodiment is excluded. Accordingly, compared with the first insertion part 2, in the first insertion part 2A, the configuration of the proximal end 2*c* is simplified and miniaturized.

In the main body part 1A, the main body optical connector 20, the PD 21, the TIA 22, and the switching circuit 23 are excluded from the main body part 1 according to the first embodiment. Accordingly, the main body part 1A has a simplified configuration with respect to the main body part 1 according to the first embodiment. As a result, compared to the main body part 1, the main body part 1A can be miniaturized and the cost can be reduced.

The PD 21 and the TIA 22 of the first insertion part 2A according to the present embodiment configure a photoelectrical conversion unit configured to perform the photoelectrical conversion at the first proximal end part to generate the first video electrical signal.

The first insertion part electrical connector 50 and the main body electrical connector 10 configure an electrical connector configured to transmit electrical signals including the first video electrical signal generated by the first photoelectrical conversion unit and the first non-video electrical signal.

As shown in FIG. 6, according to the present embodiment, a first video signal transmission unit Ti1A is configured by the VCSEL 62, the VCSEL driver 63, the optical fiber 61, the PD 21, the TIA 22, and the wiring M4, and the first video signal transmission unit Ti1A is configured to convert the video output signal of the first image sensor into the optical signal at the first distal end part, optically transmit the optical signal to the first proximal end part along the insertion direction and output the first video signal formed from the first video electrical signal that is generated by performing photoelectrical conversion with respect to the optical signal.

As the same as the first embodiment, the main body part 1A includes the main body part electrical connector 10 and the wire connecting part 30. Accordingly, as shown in FIG. 9, the endoscope 102A is configured by attaching the second insertion part 202 according to the first embodiment to the main body part 1A instead of the first insertion part 2A of the endoscope device 101A.

In the endoscope device 102A, the second video signal Sot whose signal level is corrected by the equalizer is transmitted to the limiting amplifier 24 through the second insertion part electrical connector 2500, [CMOS output signal +(−)] terminals of the main body part electrical connector 10, and the wiring m4.

Accordingly, the endoscope device 102A can display an image of the subject and the like as the same as the endoscope device 102 according to the first embodiment.

According to the above description, the endoscope device 101A according to the present embodiment includes the main body part electrical connector 10 in the main body part 1A. The main body part electrical connector 10 can be connected to the first insertion part electrical connector 50 and the second insertion part electrical connector 250. The video output signal Si from the first insertion part 2A is optically transmitted as the optical signal L in the first insertion part 2, then converted to the voltage signal at the proximal end part 2*b*, and the converted voltage signal is metallically transmitted to the main body part 1A as the first video signal Sol via the main body part electrical connector 10. The signal level of each frequency of the video output signal Si from the second insertion part 202 is corrected by the equalizer 64, and then metallically transmitted as the second video signal Sot to the main body part 1A through the second insertion part electrical connector 250 and the main body part electrical connector 10.

Accordingly, the main body part 1A is free to exchange with the first insertion part 2A having the optical transmission path or the second insertion part 202 only having the metal transmission path. The main body part 1A can exchange the connection opponent with the first insertion part 2A and the second insertion part 202 as necessary to display the video of the subject and store the video of the subject.

In the present embodiment, the main body part electrical connector 10 as the main body part connector and the first insertion part electrical connector 50 as the first insertion part connector configure a connector part used for the signal transmission of the first video signal and the first non-video electrical signal when the main body part connector is connected with the first insertion part connector.

The first insertion part 2A, the second insertion part 202, and the main body part 1 according to the present embodiment can configure the endoscope device 101A and the endoscope device 102A by connecting the exchangeable first insertion part 2A and the second insertion part 202 with the main body part 1, and the first insertion part 2A, the second insertion part 202, and the main body part 1 form an endoscope system according to the present embodiment.

Third Embodiment

An endoscope device and an endoscope system according to a third embodiment of the present invention will be described.

Figure 10:
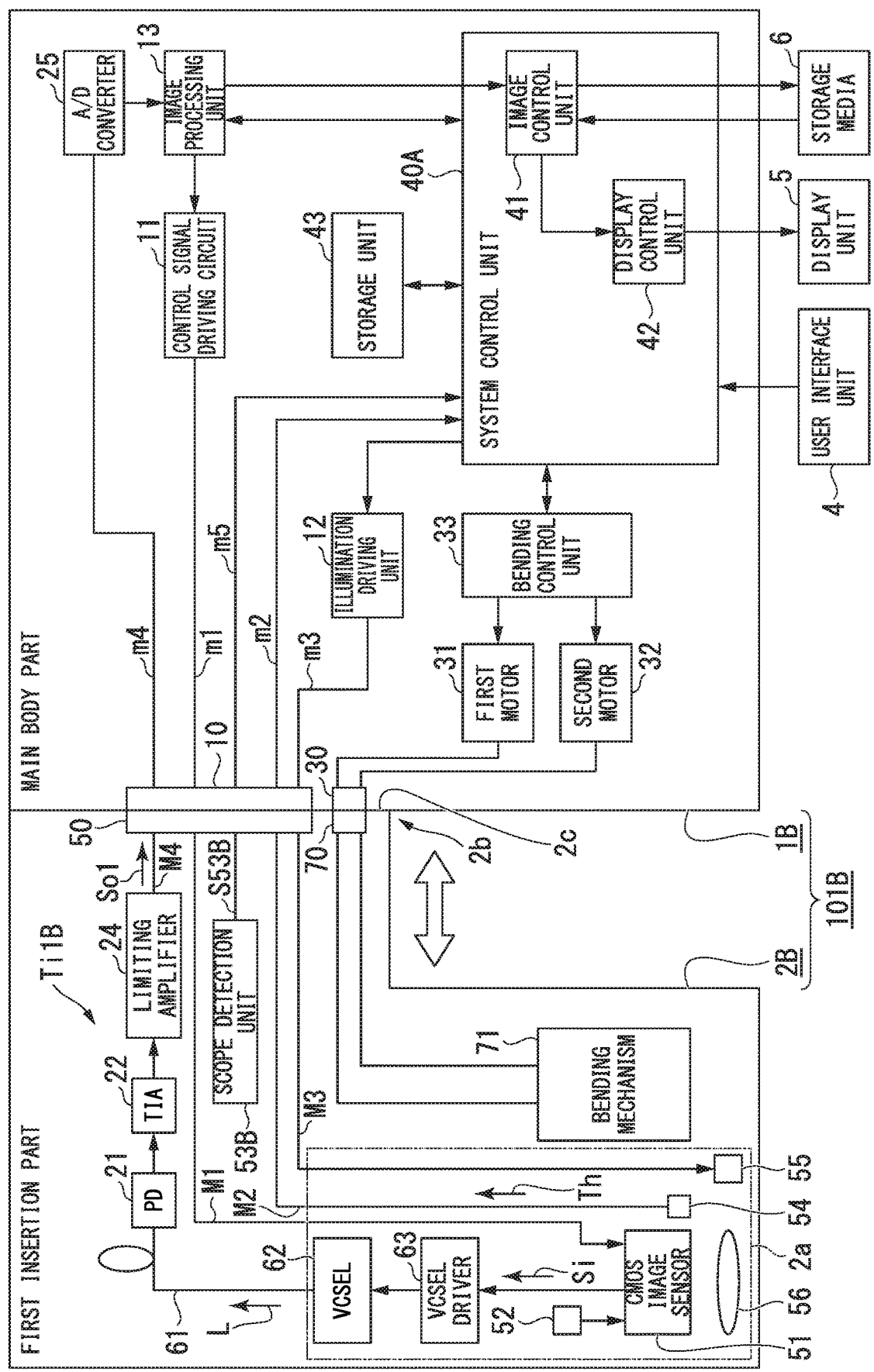
FIG. 10 is a block diagram showing a configuration example of an endoscope device according to a third embodiment of the present invention.
Figure 11:
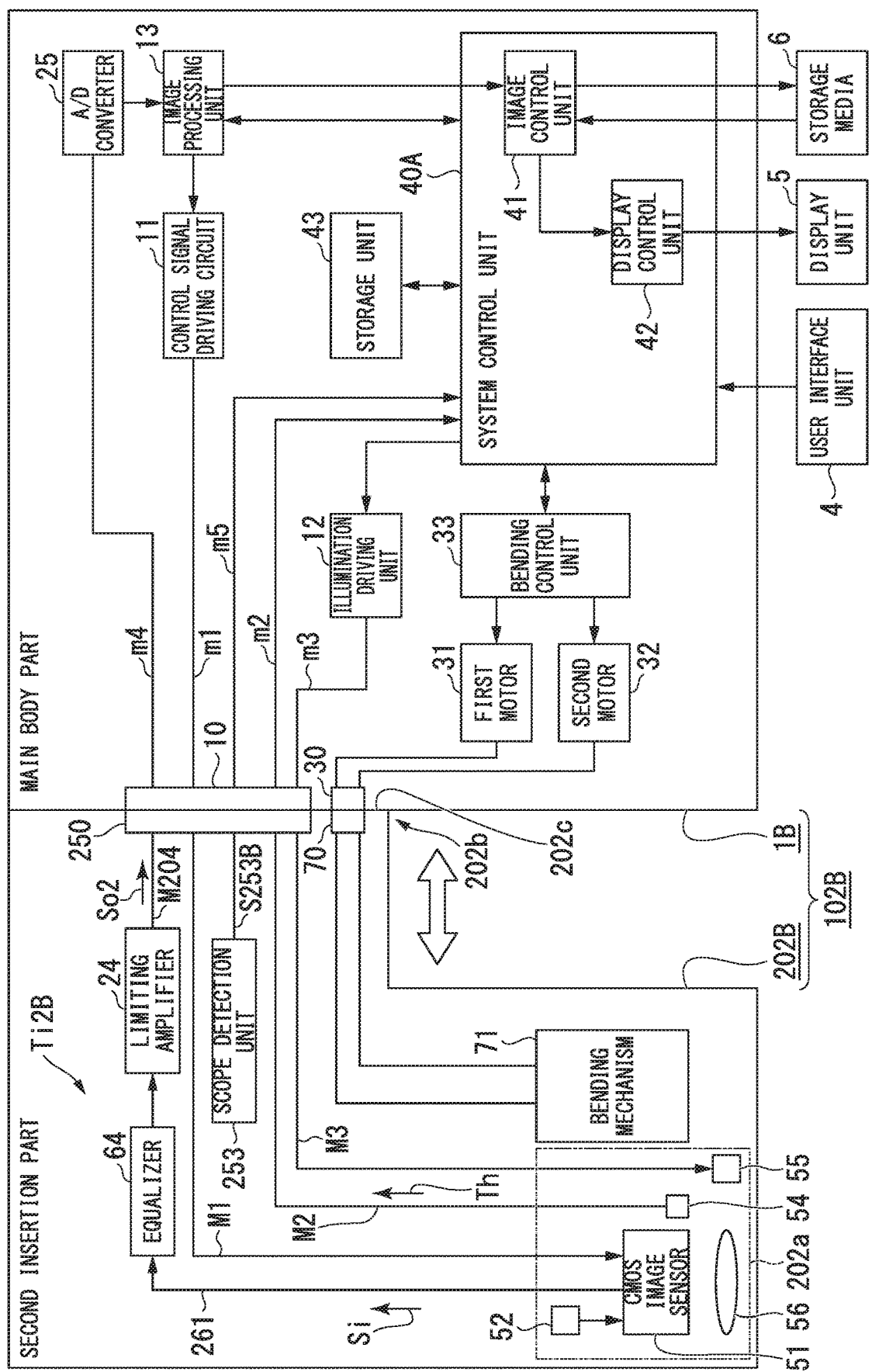
FIG. 11 is a block diagram showing a configuration example of attaching a second insertion part to a main body part of an endoscope system according to the third embodiment of the present invention.

FIG. 10 is a block diagram showing a configuration example of an endoscope device according to the third embodiment of the present invention. FIG. 11 is a block diagram showing a configuration example of attaching a second insertion part to a main body part of an endoscope system according to the third embodiment of the present invention.

As shown in FIG. 10, an endoscope device 101B according to the present embodiment includes a first insertion part 2B and a main body part 1B instead of the first insertion part 2A and the main body part 1A of the endoscope device 101A according to the second embodiment.

The first insertion part 2B includes a scope detection unit 53B instead of the scope detection unit 53A at the first insertion part 2A according to the second embodiment, and the first insertion part 2B further includes the limiting amplifier 24.

The main body part 1B is configured by excluding the limiting amplifier 24 according to the second embodiment.

The configuration of the endoscope device 101B will be described with a focus on the difference with the second embodiment.

The scope detection unit 53B is configured to generate a scope detection signal S53B. The scope detection signal S53B is generated for informing the main body part 1B with the type of the first insertion part 2B. The scope detection unit 53B has the same configuration with that of the scope detection unit 53A according to the second embodiment except that the generated signal is different.

The scope detection signal S53B at least includes information regarding a length of non-video electrical signal transmission path as the same as the scope detection signal S53A.

The limiting amplifier 24 according to the present embodiment is disposed at a proximal end part 2b of the first insertion part 2B. The limiting amplifier 24 according to the present embodiment is configured to amplify each frequency component of the signal output from the TIA 22 with a flat high gain such that an eye pattern opens.

Output terminals of the limiting amplifier 24 are connected to [CMOS output signal +(−)] terminals (not shown) of the first insertion electrical connector 50 via the wiring M4 as the same as the output terminals of the TIA 22 according to the second embodiment.

Accordingly, voltage signal whose signal level is corrected by the limiting amplifier 24 is metallically transmitted to the main body part 1B as a first video signal Sol (first video electrical signal) via the [CMOS output signal +(−)] terminals (not shown).

In the main body part 1B, the limiting amplifier 24 at the main body part 1A according to the second embodiment is excluded. Accordingly, in the main body part 1B, the [CMOS output signal +(−)] terminals (not shown) of the main body part electrical connector 10 are wired to the A/D conversion unit 25 via the wiring m4.

In the endoscope device 101B, the limiting amplifier 24 that is disposed between the main body part electrical connector 10 and the A/D conversion unit 25 of the main body part 1A according to the second embodiment is moved to a position between the TIA 22 and the first insertion part electrical connector 50 at the proximal end part 2b of the first insertion part 2B.

Accordingly, a ratio of a metal transmission to the transmission path of the video output signal Si and the first video signal Sol is extremely small as the same as the first insertion part 2A according to the second embodiment.

On the other hand, a length of the non-video electrical signal transmission path at the first insertion part 2B is the same as that of the non-video electrical signal transmission path according to the second embodiment.

As a result, in the endoscope device 101B, even if a video signal displaying a high-resolution video is transmitted through a transmission path having a length near 30 meters, a high-quality image of the video can be displayed, as the same as the endoscope device 101A according to the second embodiment.

Particularly, in the endoscope device 101B, the voltage signal output from the TIA 22 is amplified by the limiting amplifier 24 and then transmitted to the first insertion part electrical connector 50 and the main body electrical connector 10. As a result, compared to a case that the voltage signal is transmitted through the first insertion part electrical connector 50 and the main body electrical connector 10 without being amplified by the limiting amplifier 24, in the first insertion part 2B, the signal can be transmitted to the main body part 1B in a state with less signal deterioration.

The limiting amplifier 24 at the first insertion part 2B according to the present embodiment is configured to form a first amplifier unit for amplifying the first video electrical signal generated by the first photoelectrical conversion unit at the first proximal end part.

As shown in FIG. 10, according to the present embodiment, the VCSEL 62, the VCSEL driver 63, the optical fiber 61, the PD 21, the TIA 22, the limiting amplifier 24, and the wiring m4 are configured to form a first video signal transmission unit Ti1B. The first video signal transmission unit Ti1B is configured to convert the video output signal of the first image sensor into the optical signal at the first distal end part, optically transmit the optical signal to the first proximal end part along the insertion direction, and output the first video signal formed from the first video electrical signal that is generated by performing photoelectrical conversion with respect to the optical signal.

As shown in FIG. 11, the endoscope device 102B is configured by attaching the second insertion part 202B, instead of the first insertion part 2B of the endoscope device 101B, to the main body part 1B.

The second insertion part 202B is configured by adding the limiting amplifier 24 to the second insertion part 202 according to the first embodiment.

The limiting amplifier 24 at the second insertion part 202B is configured to amplify each frequency component of the signal whose signal level is corrected by the equalizer 64 with a flat high gain.

The output terminals of the limiting amplifier 24 at the second insertion part 202B are connected to [CMOS output signal +(−)] terminals (not shown) via the wiring m204.

In the endoscope device 102B, the second video signal Sot that is amplified by the limiting amplifier 24 of the second insertion part 202B is output to the A/D conversion unit 25 of the main body part 1B via the second insertion part electrical connector 250, the [CMOS output signal +(−)] terminals of the main body part electrical connector 10, and the wiring m4.

Accordingly, the endoscope device 102B can display the image of the subject as the same as the endoscope device 102A according to the second embodiment.

As shown in FIG. 11, in the present embodiment, the connecting cable 261, the equalizer 64, the limiting amplifier 24, and the wiring M204 are configured to form the second video signal transmission unit Ti2B. The second video signal transmission unit Ti2B is configured to metallically transmit the video output signal of the second image sensor to the second proximal end part along the insertion direction as the second video signal.

As the above description, the endoscope device 101B according to the present embodiment includes the main body part electrical connector 10 at the main body part 1B. The main body part electrical connector 10 is connected to the first insertion part electrical connector 50 and the second insertion part electrical connector 250. The video output signal Si from the first insertion part 2B is optically transmitted as the optical signal L in the first insertion part 2B, subsequently converted to the voltage signal at the proximal end part 2b, and then the amplified voltage signal is metallically transmitted in the main body part 1B via the main body part electrical connector 10 as the first video signal Sol. The video output signal Si from the second insertion part 202B is metallically transmitted in the main body part 1B via the second insertion part electrical connector 250 and the main body part electrical connector 10 as the second video signal Sot that is amplified by the limiting amplifier 24.

Accordingly, the main body part 1B is free to exchange with the first insertion part 2B having the optical transmission path and the second insertion part 202B only having the metal transmission path. The main body part 1B can exchange the connection opponent with the first insertion part 2B and the second insertion part 202B as necessary to display the video of the subject and store the video of the subject.

The first insertion part 2B, the second insertion part 202B, and the main body part 1B according to the present embodiment can configure the endoscope device 101B and the endoscope device 102B by connecting the exchangeable first insertion part 2B and the second insertion part 202B with the main body part 1B, and the first insertion part 2B, the second insertion part 202B, and the main body part 1B form an endoscope system according to the present embodiment.

Fourth Embodiment

An endoscope device and an endoscope system according to a fourth embodiment of the present invention will be described.

Figure 12:
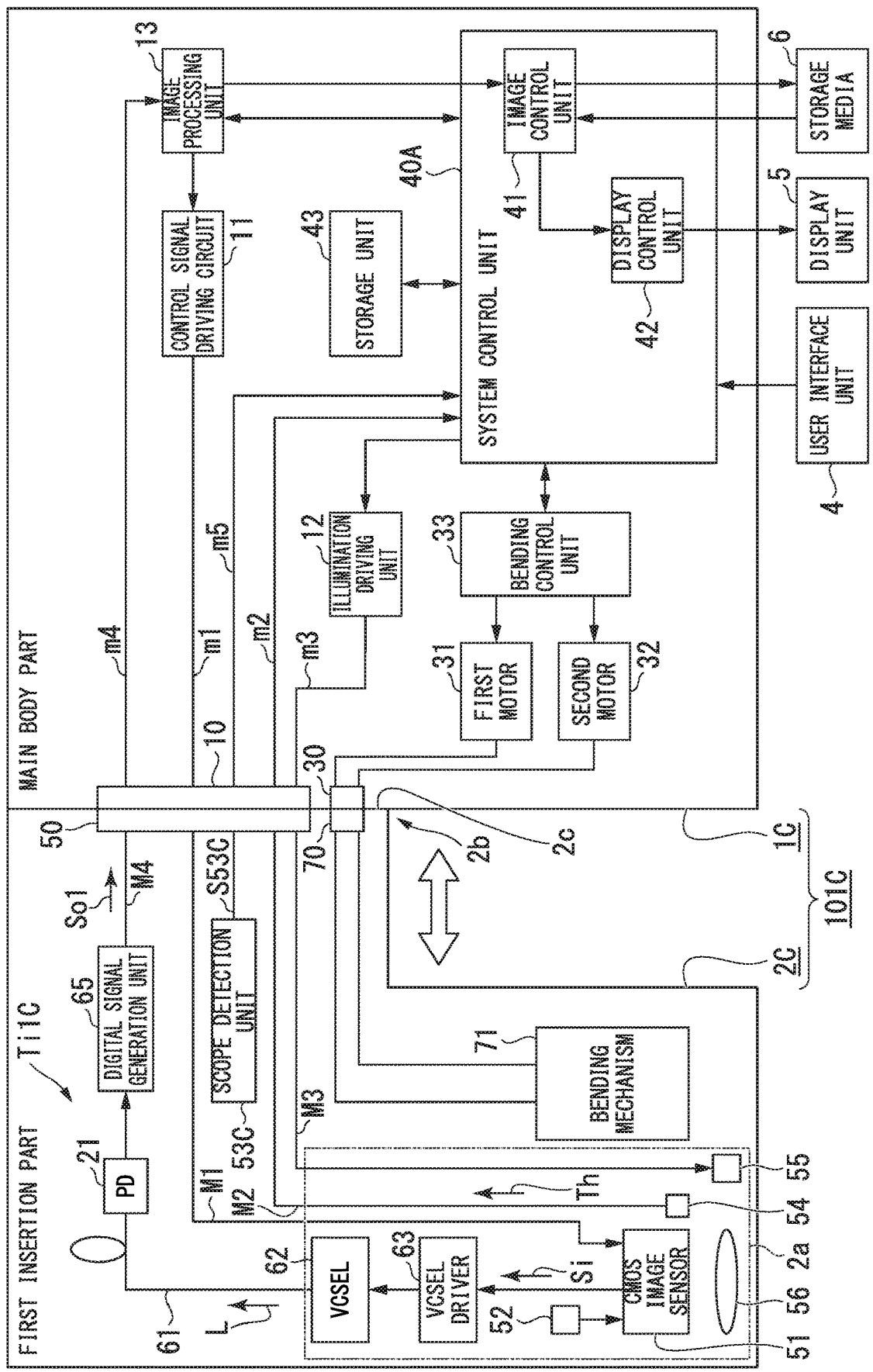
FIG. 12 is a block diagram showing a configuration example of an endoscope device according to a fourth embodiment of the present invention.
Figure 13:
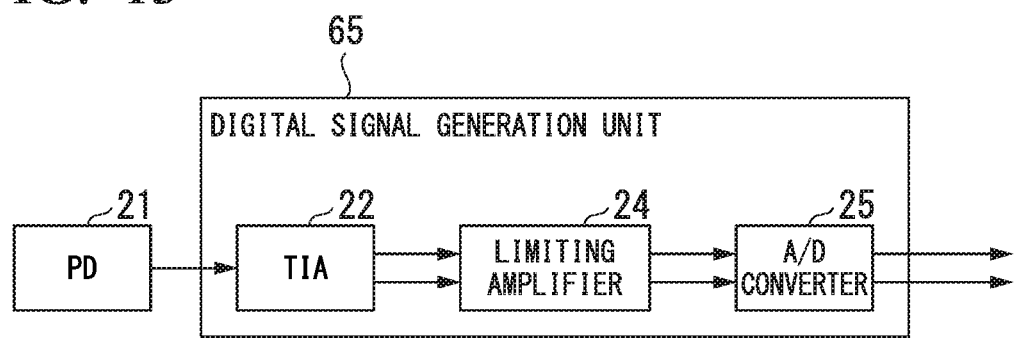
FIG. 13 is a block diagram showing a configuration example of a digital signal generation unit of the endoscope device according to the fourth embodiment of the present invention.
Figure 14:
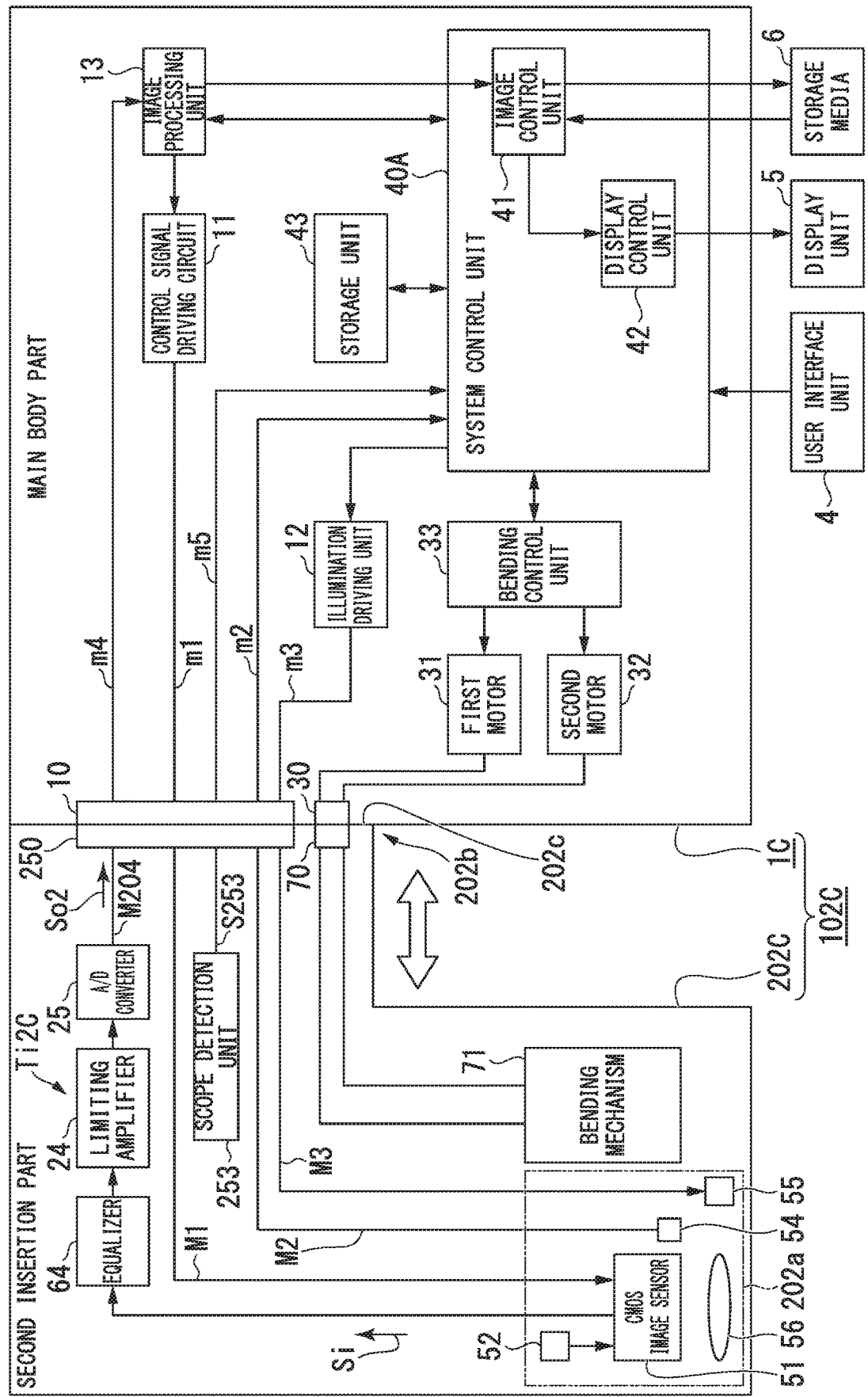
FIG. 14 is a block diagram showing a configuration example of attaching a second insertion part to a main body part of an endoscope system according to the fourth embodiment of the present invention.

FIG. 12 is a block diagram showing a configuration example of an endoscope device and an endoscope system according to the fourth embodiment of the present invention. FIG. 13 is a block diagram showing a configuration example of a digital signal generation unit of the endoscope device according to the fourth embodiment of the present invention. FIG. 14 is a block diagram showing a configuration example of attaching a second insertion part to a main body part of the endoscope system according to the fourth embodiment of the present invention.

As shown in FIG. 12, an endoscope device 101C according to the present embodiment includes a first insertion part 2C and a main body part 1C instead of the first insertion part 2B and the main body part 1B of the endoscope device 101B according to the third embodiment.

The first insertion part 3C includes a scope detection unit 53C and a digital signal generation unit 65 instead of the scope detection unit 53B, the TIA 22, the limiting amplifier 24 at the first insertion part 2B according to the third embodiment.

As shown in FIG. 13, the digital signal generation unit 65 is configured to be connected to the TIA 22, the limiting amplifier 24, and the A/D conversion unit 25 in series.

Accordingly, the first insertion part 2C includes the scope detection unit 53C instead of the scope detection unit 53B at the first insertion part 2B according to the third embodiment and further includes the A/D conversion unit 25.

The main body part 1C is configured by excluding the A/D conversion unit 25 according to the third embodiment.

The configuration of the endoscope device 101C will be described with the focus on the difference from the third embodiment.

The scope detection unit 53C is apart configured to generate a scope detection signal S53C. The scope detection signal S53C is generated for informing the main body part 1B with the type of the first insertion part 2C. The scope detection unit 53C has the same configuration as that of the scope detection unit 53B according to the third embodiment except for that the generated signal is different.

The scope detection signal S53C at least includes information regarding a length of the non-video electrical signal transmission path, as the same as the scope detection signal S53B.

The A/D conversion unit 25 according to the present embodiment is disposed at a proximal end part 2b of the first insertion part 2C. The A/D conversion unit 25 according to the present embodiment is configured to perform an A/D conversion with respect to the signal amplified by the limiting amplifier 24 to generate a digital signal.

Output terminals of the A/D conversion unit 25 are connected to [CMOS output signal +(−)] terminals (not shown) at the first insertion part electrical connector 50 via the wiring M4, as the same as the output terminals of the limiting amplifier 24 according to the third embodiment.

Accordingly, the digital single generated by the A/D conversion unit 25 is metallically transmitted to the main body part 1C via the [CMOS output signal +(−)] terminals (not shown).

In the main body part 1C, the A/D conversion unit 25 according to the third embodiment is excluded. Accordingly, in the main body part 1C, the [CMOS output signal +(−)] terminals (not shown) of the main body part electrical connector 10 are wired to the image processing unit 13 via the wiring m4.

In the endoscope device 101C, the A/D conversion unit 25 that is disposed between the main body part electrical connector 10 and the image processing unit 13 of the main body part 1B according to the third embodiment is moved to a position between the limiting amplifier 24 and the first insertion part electrical connector 50 at the proximal end part 2b of the first insertion part 2C.

Accordingly, a ratio of the metal transmission path to the transmission path of the video output signal Si and the first video signal Sol is extremely small, as the same as the first insertion part 2B according to the third embodiment.

On the other hand, in the first insertion part 2C, the length of the non-video electrical signal transmission path is the same as in the third embodiment.

As a result, in the endoscope device 101C, even if a video signal displaying a high-resolution video is transmitted through a transmission path having a length near 30 meters, a high-quality image of the video can be displayed, as the same as the endoscope device 101B according to the third embodiment.

Particularly, in the endoscope device 101C, the voltage signal output from the TIA 22 is amplified by the limiting amplifier 24 and converted into digital signal by the A/D conversion unit 25, and then transmitted to the first insertion part electrical connector 50 and the main body electrical connector 10. As a result, compared to a case that the voltage signal is transmitted through the first insertion part electrical connector 50 and the main body electrical connector 10 without being converted to the digital signal, the signal can be transmitted to the main body part 1C in a state with less signal deterioration.

At the first proximal end part, the A/D conversion unit 25 of the first insertion part 2C according to the present embodiment includes a first A/D conversion element configured to perform A/D conversion with respect to the first video electrical signal that is amplified by a first amplifier unit.

As shown in FIG. 12, according to the present embodiment, the VCSEL 62, the VCSEL driver 63, the optical fiber 61, the PD 21, the TIA 22, the limiting amplifier 24, and the wiring M4 are configured to forma first video signal transmission unit Ti1C. The first video signal transmission unit Ti1C is configured to convert the video output signal of the first image sensor into the optical signal at the first distal end part, optically transmit the optical signal to the first proximal end part along the insertion direction, and output the first video signal formed from the first video electrical signal that is generated by performing photoelectrical conversion with respect to the optical signal.

As shown in FIG. 14, the endoscope device 102C is configured by attaching the second insertion part 202C to the main body part 1C instead of the first insertion part 2C of the endoscope device 101C.

The second insertion part 202C is configured by adding the A/D conversion unit 25 to the second insertion part 202B according to the third embodiment.

The A/D conversion unit 25 at the second insertion part 202C is configured to perform A/D conversion with respect to the signal amplified by the limiting amplifier 24 to generate digital signal.

Output terminals of the A/D conversion unit 25 at the second insertion part 202C are connected to [CMOS output signal +(−)] terminals (not shown) via the wiring M204.

In the endoscope device 102C, the digitalized signal by the A/D conversion unit 25 of the second insertion part 202C is transmitted to the image processing unit 13 of the main body part 1C via the second insertion part electrical connector 250, the [CMOS output signal +(−)] terminals of the main body part electrical connector 10, and the wiring m4.

Accordingly, the endoscope device 102C can display the image of the subject as the same as the endoscope device 102B according to the third embodiment.

As shown in FIG. 14, in the present embodiment, the connecting cable 261, the equalizer 64, the limiting amplifier 24, and the wiring M204 are configured to form the second video signal transmission unit Ti2C. The second video signal transmission unit Ti2C is configured to metallically transmit the video output signal of the second image sensor to the second proximal end part along the insertion direction as the second video signal.

As the above description, the endoscope device 101C according to the present embodiment includes the main body part electrical connector 10 at the main body part 1C. The main body part electrical connector 10 is connected to the first insertion part electrical connector 50 and the second insertion part electrical connector 250. The video output signal Si from the first insertion part 2C is optically transmitted as the optical signal Lin the first insertion part 2C, subsequently converted to the voltage signal at the proximal end part 2b, and then the amplified voltage signal is processed by A/D conversion and metallically transmitted to the main body part 1C via the main body part electrical connector 10 as the first video signal Sol. The video output signal Si from the second insertion part 202C is metallically transmitted in the main body part 1C via the second insertion part electrical connector 250 and the main body part electrical connector 10 in a state of being amplified by the limiting amplifier 24.

Accordingly, the main body part 1C is free to exchange with the first insertion part 2C having the optical transmission path and the second insertion part 202C only having the metal transmission path. The main body part 1C can exchange the connection opponent with the first insertion part 2C and the second insertion part 202C as necessary to display the video of the subject and store the video of the subject.

The first insertion part 2C, the second insertion part 202C, and the main body part 1C according to the present embodiment can configure the endoscope device 101C and the endoscope device 102C by connecting the exchangeable first insertion part 2C and the second insertion part 202C with the main body part 1C, and the first insertion part 2C, the second insertion part 202C, and the main body part 1C form an endoscope system according to the present embodiment.

In the above description of each embodiment, an example that the length of the transmission path of the first insertion part having the optical transmission path is longer than that of the transmission path of the second insertion part is described. However, the length of the transmission path of each insertion part only has to be determined according to the signal transmission characteristic. The length of the first insertion part may be equal to or shorter than that of the second insertion part.

For example, the resolution of the image sensor is higher, the signal frequency becomes higher, thus, the length of the transmission path through which the metallically transmission is possible becomes shorter. Accordingly, the endoscope system may include a first insertion part configured for inspection using a high-resolution video and a second insertion part configured to have the same length with that of the first insertion part and inspect by using a low-resolution video.

In the above description of each embodiment, an example that both the first insertion part and the second insertion part have CMOS image sensor is described. However, the image sensor is not limited to the CMOS image sensor. For example, the image sensor may be implemented by a CCD sensor.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. An endoscope system, comprising:
   a main body part comprising:
      a system controller;
      a main body part connector; and
      a switching circuit comprising a first input port, a second input port and an output port;
   a first insertion part having a first tubular shape, the first insertion part comprising:
      a first image sensor disposed at a distal side of the first tubular shape;
      a first scope detector configured to:
         detect connection of the first insertion part to the main body part; and
         generate a first scope detection signal in response to detecting the connection of the first insertion part to the main body part;
      a first video signal transmission device configured to:
         convert a video output signal from the first image sensor into an optical signal at the distal side of the first tubular shape; and
         optically transmit the optical signal to a proximal side of the first tubular shape; and
      a first insertion part connector disposed at the proximal side of the first tubular shape, wherein the first insertion part connector is configured to be selectively attachable to the main body part connector, and to output the optical signal optically transmitted to the proximal side of the first tubular shape to the main body part via the main body part connector that is selectively attached to the first insertion part connector;

a second insertion part having a second tubular shape, the second insertion part comprising:
- a second image sensor disposed at a distal side of the second tubular shape;
- a second scope detector configured to:
  - detect connection of the second insertion part to the main body part; and
  - generate a second scope detection signal in response to detecting the connection of the second insertion part to the main body part;
- a second video signal transmission device configured to metallically transmit a video output signal from the second image sensor from the distal side of the second tubular shape to a proximal side of the second tubular shape; and
- a second insertion part connector disposed at the proximal side of the second tubular shape, wherein the second insertion part connector is configured to be selectively attachable to the main body part connector, and to output the video output signal metallically transmitted to the proximal side of the second tubular shape to the main body part via the main body part connector that is selectively attached to the second insertion part connector, wherein the system controller is configured to:
- generate a first control signal in response to the first scope detection signal; and
- generate a second control signal in response to the second scope detection signal, and wherein the switching circuit is configured to selectively switch between:
- receiving a signal corresponding to the optical signal received by the main body part connector through the first input port and outputting the signal corresponding to the optical signal to the output port, in response to the first control signal generated by the system controller; and
- receiving the video output signal received by the main body part connector through the second input port and outputting the video output signal to the output port, in response to the second control signal generated by the system controller.

2. The endoscope system according to claim 1,
wherein the first insertion part further comprises a first non-video electrical signal transmission device configured to metallically transmit a first non-video electrical signal, received from the main body part, from the proximal side of the first tubular shape to the first image sensor, wherein the first non-video electrical signal includes a control signal of the first image sensor,
wherein the second insertion part further comprises a second non-video electrical signal transmission device configured to metallically transmit a second non-video electrical signal, received from the main body part, from the proximal side of the second tubular shape to the second image sensor, wherein the second non-video electrical signal includes a control signal of the second image sensor,
wherein the main body part connector is configured to transmit the first non-video electrical signal from the main body part to the first insertion part, when the first insertion part connector is electrically coupled with the main body part connector, and
wherein the main body part connector is configured to transmit the second non-video electrical signal from the main body part to the second insertion part, when the second insertion part connector is electrically coupled with the main body part connector.

3. The endoscope system according to claim 2,
wherein the first non-video electrical signal transmission device is configured to transmit the first scope detection signal, and
wherein the second non-video electrical signal transmission device is configured to transmit the second scope detection signal.

4. The endoscope system according to claim 1,
wherein the first scope detection signal includes one or more of information corresponding to a length of the first insertion part, information corresponding to a formation of the first insertion part, and information corresponding to a transmission manner of the first video signal transmission device, and
wherein the second scope detection signal includes one or more of information corresponding to a length of the second insertion part, information corresponding to a formation of the second insertion part, and information corresponding to a transmission manner of the second video signal transmission device.

5. An endoscope system comprising:
a main body part comprising:
- a system controller;
- a main body part connector; and
- a switching circuit comprising a first input port, a second input port and an output port, wherein the main body part is configured to be selectively connected to a first insertion part having a first tubular shape, the first insertion part comprising:
- a first image sensor disposed at a distal side of the first tubular shape;
- a first scope detector configured to:
  - detect connection of the first insertion part to the main body part; and
  - generate a first scope detection signal in response to detecting the connection of the first insertion part to the main body part;
- a first video signal transmission device configured to:
  - convert a video output signal from the first image sensor into an optical signal at the distal side of the first tubular shape; and
  - optically transmit the optical signal to a proximal side of the first tubular shape; and
- a first insertion part connector disposed at the proximal side of the first tubular shape, wherein the first insertion part connector is configured to be selectively attachable to the main body part connector, and to output the optical signal optically transmitted to the proximal side of the first tubular shape to the main body part via the main body part connector that is selectively attached to the first insertion part connector, wherein the main body part is configured to be selectively connected to a second insertion part having a second tubular shape, the second insertion part comprising:
- a second image sensor disposed at a distal side of the second tubular shape;
- a second scope detector configured to:
  - detect connection of the second insertion part to the main body part; and generate a second scope detection signal in response to detecting the connection of the second insertion part to the main body part;

a second video signal transmission device configured to metallically transmit a video output signal from the second image sensor from the distal side of the second tubular shape to a proximal side of the second tubular shape; and a second insertion part connector disposed at the proximal side of the second tubular shape, wherein the second insertion part connector is configured to be selectively attachable to the main body part connector, and to output the video output signal metallically transmitted to the proximal side of the second tubular shape to the main body part via the main body part connector that is selectively attached to the second insertion part connector, wherein the system controller is configured to:
    generate a first control signal in response to the first scope detection signal; and
    generate a second control signal in response to the second scope detection signal, and wherein the switching circuit is configured to selectively switch between:
    receiving a signal corresponding to the optical signal received by the main body part connector through the first input port and outputting the signal corresponding to the optical signal to the output port, in response to the first control signal generated by the system controller; and
    receiving the video output signal received by the main body part connector through the second input port and outputting the video output signal to the output port, in response to the second control signal generated by the system controller.

\* \* \* \* \*